(12) United States Patent
Nakatani et al.

(10) Patent No.: US 8,911,947 B2
(45) Date of Patent: Dec. 16, 2014

(54) DNA FRAGMENT USED AS ATTACHED TO 5' END OF PRIMER USED IN NUCLEIC ACID AMPLIFICATION REACTION AND USE OF DNA FRAGMENT

(75) Inventors: Kazuhiko Nakatani, Suita (JP); Fumie Takei, Suita (JP); Masaki Hagihara, Suita (JP)

(73) Assignee: Furukawa Electric Advanced Engineering Co., Ltd., Chiba (JP)

( * ) Notice: Subject to any disclaimer, the term of this patent is extended or adjusted under 35 U.S.C. 154(b) by 868 days.

(21) Appl. No.: 12/439,515

(22) PCT Filed: Aug. 28, 2007

(86) PCT No.: PCT/JP2007/066650
§ 371 (c)(1),
(2), (4) Date: Feb. 27, 2009

(87) PCT Pub. No.: WO2008/026582
PCT Pub. Date: Mar. 6, 2008

(65) Prior Publication Data
US 2010/0015618 A1    Jan. 21, 2010

(30) Foreign Application Priority Data
Sep. 1, 2006 (JP) .................................. 2006-238299

(51) Int. Cl.
*C12Q 1/68*    (2006.01)
*C07H 21/04*    (2006.01)
(52) U.S. Cl.
CPC .............. *C12Q 1/6858* (2013.01); *C12Q 1/686* (2013.01); *C12Q 2600/156* (2013.01)
USPC ....................... 435/6.12; 536/24.33
(58) Field of Classification Search
None
See application file for complete search history.

(56) References Cited

U.S. PATENT DOCUMENTS 6,548,250 B1    4/2003    Sorge
2002/0182622 A1    12/2002    Nakamura et al.
(Continued)

FOREIGN PATENT DOCUMENTS

JP    2001-089478 A    4/2001
JP    2003-052372 A    2/2003
(Continued)

OTHER PUBLICATIONS

GenBank GI:212551134 [online] Feb. 14, 2013 [retrieved on Jan. 21, 2014] retrieved from http://www.ncbi.nlm.nih.gov/nuccore/212551134.*

(Continued)

*Primary Examiner* — Samuel Woolwine
(74) *Attorney, Agent, or Firm* — Morrison & Foerster LLP

(57) ABSTRACT

A method is provided which enables quick, convenient, inexpensive, and high sensitivity confirmation of nucleic acid amplification after a nucleic acid amplification reaction. The DNA fragment in accordance with the present invention is a single-stranded DNA fragment containing a hairpin structure which in turn contains a bulge, wherein the DNA fragment is used as being attached to the 5' end of a primer used in nucleic acid amplification. The nucleic acid amplification confirmation method in accordance with the present invention quantifies a hairpin primer containing the DNA fragment at its 5' end by using bulge-binding fluorescent molecules after carrying out PCR or like nucleic acid amplification reaction using the hairpin primer. SNPs are detected quickly and conveniently at low cost and with high sensitivity by applying the nucleic acid amplification confirmation method, for example, to allele specific PCR.

10 Claims, 12 Drawing Sheets

(56) References Cited

U.S. PATENT DOCUMENTS

2003/0148301 A1    8/2003   Aono et al.
2006/0014144 A1    1/2006   Christensen et al.

FOREIGN PATENT DOCUMENTS

| JP | 2003-259873 A | 9/2003 |
| JP | 2003-261567 A | 9/2003 |
| JP | 2004-262827 A | 9/2004 |
| WO | 2004/061127 A2 | 7/2004 |
| WO | 2006/032487 A2 | 3/2006 |
| WO | 2006/086502 A2 | 8/2006 |
| WO | WO-2006/082685 A1 | 8/2006 |

OTHER PUBLICATIONS

The Stratagene Catalog. p. 39. 1988.*

International Search Report mailed Oct. 9, 2007, for PCT Application No. PCT/JP2007/066650 filed Aug. 28, 2007, 2 pages.

Nazarenko, I. A. et al. (1997). "A Closed Tube Format for Amplification and Detection of DNA Based on Energy Transfer," *Nucleic Acids Research* 25(12):2516-2521.

Suda, H. et al. (2003). "Development of Bulge DNA Bonding Molecule," Chemical Society of Japan, 83rd Annual Spring Meeting, p. 1104, (English translation attached, 1 page).

Suda, H. et al. (2004). "Application of 2,7-Diamino-1,8-Naphthyridine Derivative to SNP Typing," Chemical Society of Japan, 84th Annual Spring Meeting, p. 1060. (English translation attached, 1 page).

Suda, H. et al. (2005). "N,N'-Bis(3-Aminopropyl)-2,7-Diamino-1,8-Naphthyridine Stabilized a Single Pyrimidine Bulge in Duplex DNA," *Bioorganic & Medicinal Chemistry* 13:4507-4512.

Takei, F. et al. (2007). "Allele Specific C-Bulge Probes with One Unique Fluorescent Molecule Discriminate the Single Nucleotide Polymorphism in DNA" *Chemistry—A European Journal* 13:4452-4457.

Takei, F. et al. (Mar. 13, 2006). "SNP Detection Using N,N'-(3-Aminopropyl)-2,7-Diamino-1,8-Naphthyridine," Chemical Society of Japan, 86th Annual Spring Meeting, p. 850. (English translation attached, 1 page).

Xi, Z. et al. (2005). "Selective Interaction Between Tylophorine B and Bulged DNA," *Bioorganic & Medicinal Chemsitry Letters* 15:2673-2677.

Extended European Search Report received for EP Patent Application No. 07806129.8, mailed on Aug. 24, 2010, 11 pages.

Fukusaki et al., "DNA Aptamers that Bind to Chitin", Bioorganic & Medicinal Chemistry Letters, vol. 10, No. 5, Mar. 1, 2000, pp. 423-425.

Gu et al., "DNA Damage by Thiol-Activated Neocarzinostatin Chromophore at Bulged Sites", Biochemistry, vol. 39, No. 16, Apr. 25, 2000, pp. 4881-4891.

Kofiadi et al., "Methods for Detecting Single Nucleotide Polymorphisms: Allele-Specific PCR and Hybridization with Oligonucleotide Probe", Genetika, vol. 42, No. 1, Jan. 2006, pp. 16-26.

Nakatani, "Chemistry Challenges in SNP Typing", ChemBioChem, vol. 5, No. 12, Dec. 3. 2004, pp. 1623-1633.

\* cited by examiner

FIG. 3

| Primer | PCR Primer Base Sequence and Structure |
|---|---|
| takei 5<br>SEQ ID NO:6 | 5' ATCAA_ACACAC⤵T-T<br>3' CAGTATCGACAAAGGAC-TAGTTCTGT_TG⤴T-T |
| takei 18<br>SEQ ID NO:7 | 5' ATCA_ACATCTCA_AC⤵T-T<br>3' CAGTATCGACAAAGGAC-TAGTCTGTA_AGTCTG⤴T-T |
| takei 18-4<br>SEQ ID NO:8 | 5' ATCATCTACA_AC⤵T-T<br>3' CAGTATCGACAAAGGAC-TAGTA_ATGTCTG⤴T-T |
| takei 2<br>SEQ ID NO:9 | 5' CATCCAA_ACAACCA⤵T-T<br>3' CAGTATCGACAAAGGAC-GTAGGTTCTGTTGGT⤴T-T |
| takei 2-2<br>SEQ ID NO:10 | 5' CATCCAT_TCAACCA⤵T-T<br>3' CAGTATCGACAAAGGAC-GTAGGTACAGTTGGT⤴T-T |

FIG. 8

| Primer | PCR Primer Base Sequence and Structure |
|---|---|
| takei 18-4<br>SEQ ID NO: 8 | 3'CAGTATCGACAAAGGAC5'—3'TAGTA_ATGTCTG⌒5ATCATCTACA_AC⌒T-T-T-T |
| takei 18-4A<br>SEQ ID NO: 13 | 3'AAGTATCGACAAAGGAC5'—3'TAGTA_ATGTCTG⌒5ATCATCTACA_AC⌒T-T-T-T |
| takei 18-4G<br>SEQ ID NO: 14 | 3'GAGTATCGACAAAGGAC5'—3'TAGTA_ATGTCTG⌒5ATCATCTACA_AC⌒T-T-T-T |
| takei 18-4T<br>SEQ ID NO: 15 | 3'TAGTATCGACAAAGGAC5'—3'TAGTA_ATGTCTG⌒5ATCATCTACA_AC⌒T-T-T-T |

DNA FRAGMENT USED AS ATTACHED TO 5' END OF PRIMER USED IN NUCLEIC ACID AMPLIFICATION REACTION AND USE OF DNA FRAGMENT

CROSS REFERENCE TO RELATED APPLICATIONS

This application is a U.S. National Phase application of PCT/JP2007/066650, filed Aug. 28, 2007, which claims priority to Japan Application Serial No. 2006-238299, filed Sep. 1, 2006, the contents of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322008500SubSeqList2.txt, date recorded: Jul. 30, 2014, size: 5 KB).

TECHNICAL FIELD

The present invention relates in general to DNA fragments used as being attached to the 5' end of a primer used in nucleic acid amplification reaction and use of such DNA fragments. In particular, the invention relates to DNA fragments which attach to the 5' end of a primer whereby amplification of nucleic acid is readily confirmed and relates also to hairpin primers making use thereof, methods of confirming nucleic acid amplification, methods of detecting SNPs, and reagent kits containing such DNA fragments.

BACKGROUND ART

PCR (polymerase chain reaction) and other techniques to amplify particular nucleic acids are applied in various fields in biotechnology. (Hereinafter, throughout this specification, these PCR and other nucleic acid amplification reactions will be referred to as "nucleic acid amplification reactions.")

A nucleic acid amplification reaction like PCR generally requires a process of confirming whether a target nucleic acid has been specifically amplified. (Amplification of nucleic acid by PCR or a like nucleic acid amplification method will be simply referred to as "nucleic acid amplification" throughout this specification.)

Amplification of nucleic acid is confirmed, for example, as follows: The reaction liquid having undergone PCR or a like nucleic acid amplification reaction is subjected to get electrophoresis using polyimide or another like gel. The DNA fragments obtained by the PCR amplification are then stained.

Nucleic acid amplification in a nucleic acid amplification reaction can be confirmed also by other conventional methods. For example, the turbidity of the reaction liquid having undergone a nucleic acid amplification reaction may be measured. A microarray may be used including a probe which binds specifically to target nucleic acid. Another example is real time PCR by which the amplification can be confirmed in real time by using a fluorescent-labelled probe which binds to a double-stranded DNA or specifically to a target PCR product.

The nucleic acid amplification reaction, including PCR, is used also, for example, to analyze single nucleotide polymorphisms (hereinafter, "SNPs"). The methods above are also used in these cases to confirm nucleic acid amplification.

Patent literature 1 proposes a primer for use with wildtype and one or two kinds of primers for use with mutation type simultaneously or separately acting, together with a DNA polymerase, on a chromosome or its fragment which includes an SNP site to be analyzed, in order to find if any primer-based extension has occurred. Electrophoresis is used in the analysis to confirm presence of an amplified nucleic acid.

Patent literature 2 suggests use of a universal primer and two kinds of specific primers, one for use with a reference sequence and the other for use with a mutated sequence, both of which include an SNP site, in order to amplify a target part of a sequence. This SNP analysis, similarly to patent literature 1, confirms presence of amplified product by subjecting the reaction liquid obtained to electrophoresis.

Patent literature 3 suggests use of target genome DNA and pairs of primers, in order to amplify a nucleic acid which includes an SNP site for typing. The amplified product obtained is hybridized using, for example, a labelled probe for the typing.

Quick and convenient SNP analysis would enable tailor-made medical care (for example, bedside diagnostics for the best therapy and drug administration), making promising POC (Point Of Care) technology. To achieve these goals, a method is desired which can more quickly and more conveniently confirm amplification of a nucleic acid after a nucleic acid amplification reaction.

CITATION LIST

Patent Literature 1
International Application Published under the PCT, No. WO 01/042498, (Publication Date: Jun. 14, 2001)
Patent Literature 2
Japanese Patent Application Publication, Tokukai, No. 2003-52372 (Publication Date: Feb. 25, 2003)
Patent Literature 3
Japanese Patent Application Publication, Tokukai, No. 2002-300894 (Publication Date: Oct. 15, 2002)

SUMMARY OF INVENTION

Technical Problem

A problem with the nucleic acid amplification reactions described above, including PCR, is that the confirmation of amplification of nucleic acid requires complex processes, much time, and large cost.

The method that involves electrophoresis of the reaction liquid obtained from a nucleic acid amplification reaction and subsequent staining of an amplified nucleic acid fragment takes time in the electrophoresis and staining. The method is also costly because an electrophoresis device, an electrophoresis gel, and a staining reagent are needed, to name only a few.

The method that involves measurement of the turbidity of the reaction liquid obtained from a nucleic acid amplification reaction to confirm amplification requires an extremely large amount of a nucleic acid amplification product, which makes it troublesome to set conditions for the amplification. In addition, the method is inapplicable to tiny amounts of samples.

The use of a DNA microarray requires that the probe on the microarray be labelled with, for example, a fluorescent material. Costly chips also need to be manufactured.

Real time PCR also needs, for example, a fluorescent-labelled probe. Devices and reagents for real time PCR are also expensive.

The methods suggested in patent literatures 1 and 2, as examples, are also time-consuming and costly because the methods require electrophoresis and subsequent staining of PCR-amplified DNA fragments to confirm PCR amplification as mentioned above. Meanwhile, patent literature 3 requires, apart from primers, a probe which hybridizes to a target genome. The probe further needs to be fluorescent labelled or otherwise chemically modified. The requirements make it difficult to find desirable typing conditions.

Some suggested SNP analysis methods do not involve nucleic acid amplification reactions. SNP analysis, however, has been developed as an extension of searching technology for SNPs exhaustively through huge amounts of samples (specimens) and inevitably assumes that the blood taken from a patient be transported to a laboratory or like facility where SNP analysis apparatus is available. These procedures are time-consuming, making convenient and quick SNP analysis impractical, and completely disqualify SNP analysis as POC technology. Particularly, in the wake of a virus infection that is increasingly threatening over the last few years, how quickly the infection is diagnosed is extremely important in treatment for patient's recovery. Immediate diagnosis after taking a blood sample is necessary in those cases.

The PCR and other nucleic acid amplification reactions require complex processes and a long time in the confirmation of amplification. A quick, convenient, and inexpensive method is in demand for the confirmation of amplification.

The present invention, conceived in view of the above issues, has an objective of providing a quick, convenient, and inexpensive method of confirming amplification in a nucleic acid amplification reaction and furthermore providing a quick, convenient, and inexpensive method of analyzing SNPs.

Solution to Problem

We, the inventors, have diligently worked in order to accomplish the objectives. As a result, we have found that if a hairpin primer prepared by attaching, to the 5' end of a primer used in nucleic acid amplification reaction, a DNA fragment containing a hairpin structure which in turn contains a bulge is used in nucleic acid amplification reaction, the hairpin primer loses its hairpin structure due to an extending complementary chain, and the bulge consequently disappears. We have also found that the amplification of nucleic acid can be readily confirmed by quantifying and comparing pre- and post reaction bulges using bulge-binding molecules, which has led to the completion of the invention.

A DNA fragment in accordance with the present invention is, to address the problems, characterized in that it is a single-stranded DNA fragment containing a hairpin structure which in turn contains a bulge, wherein the DNA fragment is used as being attached to a 5' end of a primer used in a nucleic acid amplification reaction.

The DNA fragment in accordance with the present invention is preferably such that the hairpin structure contains two or more bulges.

The DNA fragment in accordance with the present invention is preferably such that the or each bulge is a cytosine bulge.

The DNA fragment in accordance with the present invention is preferably such that the cytosine bulge is formed by intramolecular thymine-adenine base pairing of a thymine in a thymine-cytosine-thymine sequence and an adenine in an adenine-adenine sequence, both in the single-stranded DNA fragment.

The DNA fragment in accordance with the present invention preferably contains any one of base sequences according to SEQ ID NOs 1 to 5.

A hairpin primer in accordance with the present invention is, to address the problems, characterized by including: the DNA fragment in accordance with the present invention; and a primer, for use in the nucleic acid amplification reaction, attached to a 3' end of the DNA fragment.

The nucleic acid amplification reaction is preferably PCR.

A nucleic acid amplification confirmation method in accordance with the present invention is, to address the problems, characterized in that it is a method of confirming amplification of a nucleic acid in a nucleic acid amplification reaction and the method includes: the step of preparing a nucleic acid amplification reaction liquid containing a set of primers at least one of which is the hairpin primer in accordance with the present invention; the unreacted hairpin primer measuring step of quantifying the hairpin primer in the nucleic acid amplification reaction liquid using bulge-binding molecules; the step of carrying out the nucleic acid amplification reaction; and the reacted hairpin primer measuring step of, after the nucleic acid amplification reaction is terminated, quantifying the hairpin primer in the nucleic acid amplification reaction liquid using bulge-binding molecules.

The nucleic acid amplification confirmation method in accordance with the present invention is preferably such that the bulge-binding molecules are a compound with a naphthyridine ring.

The nucleic acid amplification confirmation method in accordance with the present invention is preferably such that the compound with a naphthyridine ring is a 2,7-diamino naphthyridine derivative of chemical formula 1:

Chem. 1

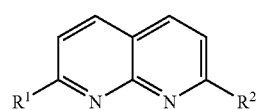

(1)

where each of $R^1$ and $R^2$, mutually independent, is a primary amine residue, a secondary amine residue, or a tertiary amine residue.

The nucleic acid amplification confirmation method in accordance with the present invention is preferably such that the 2,7-diamino naphthyridine derivative is 2,7-diamino-1,8-naphthyridine of chemical formula 2:

Chem. 2

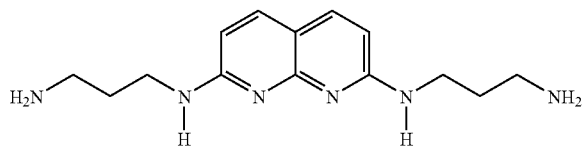

(2)

The nucleic acid amplification confirmation method in accordance with the present invention is preferably such that: the bulge-binding molecules are added to the nucleic acid amplification reaction liquid to carry out the unreacted hairpin primer measuring step; and the nucleic acid amplification reaction liquid is used as is in the nucleic acid amplification reaction in the unreacted hairpin primer measuring step.

AN SNP detection method in accordance with the present invention is, to address the problems, characterized in that the method includes the step of carrying the nucleic acid amplification confirmation method in accordance with the present invention.

The SNP detection method in accordance with the present invention is preferably such that any one of the set of primers is designed to have a 3' end located at a site where a target SNP is to be detected.

The SNP detection method in accordance with the present invention is preferably such that the primer designed to have a 3' end located at a site where a target SNP is to be detected is the hairpin primer.

The SNP detection method in accordance with the present invention is preferably such that: the nucleic acid amplification reaction liquid contains a competitor primer; the competitor primer is designed to have a 3' end located at the site where the target SNP is to be detected; and the competitor primer has, at the 3' end, a base complementary to a base in a mutated nucleic acid where the target SNP is to be detected when the hairpin primer is used to amplify a wildtype nucleic acid and a base complementary to a base in a wildtype nucleic acid where the target SNP is to be detected when the hairpin primer is used to amplify a mutated nucleic acid.

A reagent kit in accordance with the present invention is, to address the problems, is characterized in that it is a reagent kit for confirming amplification of a nucleic acid in a nucleic acid amplification reaction and the reagent kit includes at least the DNA fragment in accordance with the present invention.

Additional objectives, advantages and novel features of the invention will be set forth in part in the description which follows, and in part will become apparent to those skilled in the art upon examination of the following or may be learned by practice of the invention.

Figure 1:
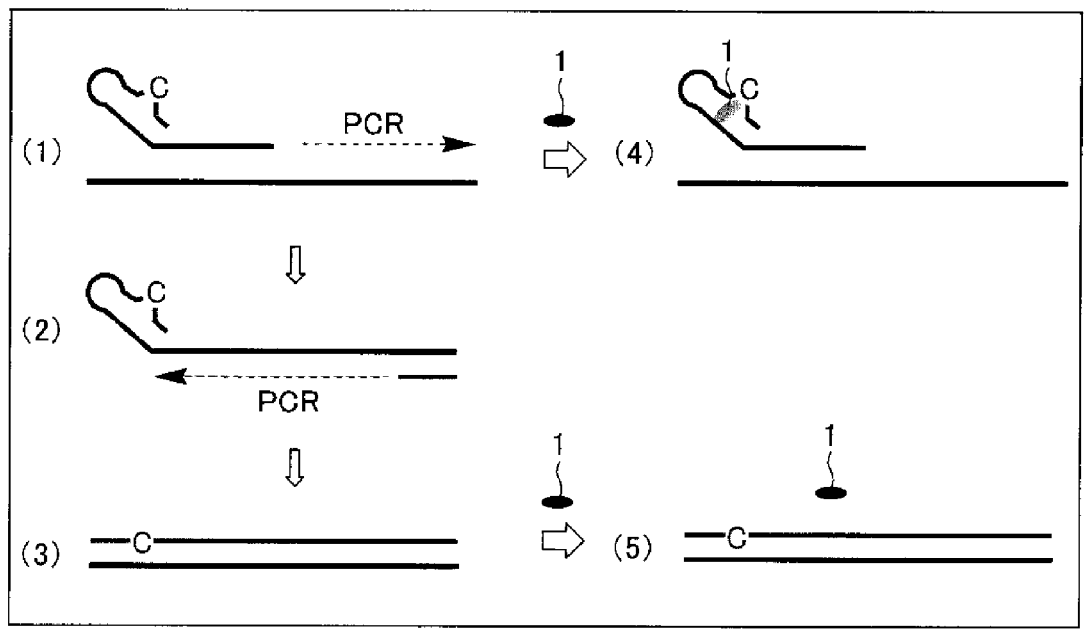
FIG. 1

A schematic drawing illustrating how a nucleic acid amplification confirmation method works according to an embodiment of the present invention.

FIG. 2

A schematic drawing illustrating how an SNP analysis method works according to an embodiment of the present invention.

FIG. 3

A schematic drawing listing the names, base sequences, and structures of the hairpin primers used in examples in accordance with the present invention.

FIG. 4

A drawing, for use in examples, showing a comparison of pre-PCR and post-PCR fluorescence intensity.

FIG. 5

A drawing, for use in examples, representing a comparison of fluorescence intensity of bulge-binding fluorescent molecules hybridized to cytosine bulges made up of different sequences.

FIG. 6

A drawing, for use in examples, representing a comparison of the relationship between PCR cycle and the fluorescence intensity of bulge-binding fluorescent molecules.

FIG. 7

A drawing, for use in examples, showing results of polyacrylamide gel electrophoresis of PCR products obtained by PCR using M13RV, takei 5, takei 18, and takei 18-4 respectively as a reverse primer.

FIG. 8

A schematic drawing listing the names, base sequences, and structures of the hairpin primers used in examples in accordance with the present invention.

FIG. 9

A drawing, for use in examples, representing a comparison of the relationship between PCR cycle and efficiency of nucleic acid amplification in allele specific PCR using hairpin primers in accordance with the present invention.

FIG. 10

A drawing, for use in examples, showing results of polyacrylamide gel electrophoresis of PCR products obtained by PCR using takei 18-4, takei 18-4A, takei 18-4G, takei 18-4T, and M13RV respectively as a reverse primer.

FIG. 11

A drawing, for use in examples, representing a comparison of the relationship between PCR cycle and efficiency of nucleic acid amplification in allele specific PCR using hairpin primers together with competitor primers in accordance with the present invention.

FIG. 12

A drawing, for use in examples, showing results of polyacrylamide gel electrophoresis of PCR products obtained by PCR using takei 18-4 and M13RVA as reverse primers and takei 18-4A and M13RV as competitor primers.

REFERENCE SINGS LIST

1 Bulge-Binding Fluorescent Molecule

DESCRIPTION OF EMBODIMENTS

The following will describe embodiments of the present invention. The description is by no means limiting the scope of the present invention. The present invention can be practised with modifications not given in the description where necessary, without departing from the spirit and scope of the present invention.

DNA Fragment in Accordance with the Present Invention

The DNA fragment in accordance with the present invention may be any single-stranded DNA fragment containing a hairpin structure which in turn contains a bulge. The DNA fragment is used as it is attached to the 5' end of a primer used in a nucleic acid amplification reaction.

The hairpin structure of the DNA fragment in accordance with the present invention is formed by a single-stranded DNA pairing intramolecularly to give an arc-shaped segment and a double-stranded segment in the DNA. The DNA fragment in accordance with the present invention contains a bulge in the double-stranded segment.

The number of bases making up the hairpin structure of the DNA fragment in accordance with the present invention is by no means limited provided that the bases are sufficient to form an arc-shaped DNA segment, a double-stranded DNA segment, and a bulge in the double-stranded DNA segment. The number is preferably from 24 to 33, more preferably from 24 to 28. If the number is greater than or equal to 24, a suitable arc-shaped DNA segment, double-stranded DNA segment, and bulge are formed. If the number is less than or equal to 33, those bases do not affect nucleic acid amplification reaction.

The base sequence in the arc-shaped DNA segment is not limited in any particular manner provided that the sequence is capable of forming the arc-shaped segment. The number of the bases is preferably from 3 to 7, more preferably 4. When the arc-shaped segment consists of four bases, the sequence is preferably TTTT because the hairpin structure containing a TTTT arc-shaped segment is readily linearized in nucleic acid amplification reaction.

The base sequence in the DNA fragment in accordance with the present invention may be designed as follows.

Base sequences, capable of pairing, are placed across another base sequence: for example, CCAAnnnnTTGG (SEQ ID NO:16) where n may be any base. In this example, a bulge base may be present anywhere in the CCAA or TTGG. In this design, the nnnn curls to form an arc-shaped segment, and the CCAA and TTGG hybridize to form a double-stranded segment, resulting in the formation of a bulge due to the presence of the bulge base.

More generally, two base sequences, capable of hybridizing to each other, are designed to be present at the respective ends of another base sequence which corresponds to the DNA forming an arc-shaped segment, and the base sequences in the hybridization region are designed to contain a bulge base. The DNA fragment in accordance with the present invention is obtainable by synthesizing a DNA fragment from the base sequences designed this way. The DNA fragment may be synthesized by any publicly known method and device. An example is chemical synthesis.

The above example dealt with a case where the DNA fragment in accordance with the present invention contained only a hairpin structure consisting of an arc-shaped DNA segment and a bulge-containing double-stranded DNA segment. The DNA fragment in accordance with the present invention most preferably contains only a hairpin structure as in the example. The invention however still works if a nucleic acid is attached to the 3' and/or the 5' end of the hairpin structure. In these alternative cases, the number of bases is preferably from 1 to 20 at both the 3' and 5' ends. When the number is in this range, nucleic acid amplification reaction is not affected.

Throughout this specification, the "bulge" refers to a swelling caused by the presence of an excess base in one of the strands of the double-stranded DNA segment. For example, if a DNA fragment containing a TCT sequence and an AA sequence folds to form a hairpin structure so that the TCT and AA sequences are positioned facing each other, the two Ts in the TCT sequence pairs with the two As in the AA sequence. As a result, the C between the two Ts cannot find a base for pairing and forms a swell on the strand. This swelling structure is the bulge. The bulge formed by an excess C (cytosine) as in this example will be referred to as the cytosine bulge throughout this specification. The same terminology applies to A (adenine), G (guanine), and T (thymine): e.g., an "adenine bulge." The "bulge base" refers to the excess base in the bulge throughout this specification.

Number of Bulges

The DNA fragment in accordance with the present invention may contain only one bulge and preferably 2 or more bulges, more preferably 2 to 4 bulges. The presence of plural bulges adds to the sites to which bulge-binding molecules (detailed later) can bind. That in turn enables high sensitivity detection by means of the hairpin primer.

When plural bulges are present, any adjacent bulge bases are separated preferably by 3 to 5 bases, more preferably by 4 bases. If two bulges are located too closely, the binding of bulge-binding molecules to the bulges (detailed later) is disrupted. If the bulge bases are separated by too great a distance, the hairpin structure is destabilized, and the hairpin is not linearized in a satisfactory manner. In addition, the DNA fragment in accordance with the present invention becomes too large, which adds to synthesis cost.

Types of Bulges and their Sequences

The bulge in the DNA fragment in accordance with the present invention may be any one of an adenine bulge, a cytosine bulge, a thymine bulge, and a guanine bulge.

When the bulge is either a thymine bulge or a cytosine bulge, the local absorption maximum wavelength for fluorescence intensity of the fluorescent molecule shifts if a compound containing a naphthyridine ring (detailed later) binds to the bulge. Therefore, nucleic acid amplification is confirmed if the fluorescence at the post-shifting local absorption maximum wavelength decreases over the course of nucleic acid amplification reaction.

On the other hand, when the bulge is either an adenine bulge or a guanine bulge, the compound containing a naphthyridine ring (detailed later) fluoresces if the compound does not bind to a bulge and does not fluoresce if the compound binds to the bulge. Therefore, nucleic acid amplification is confirmed if the fluorescence increases over the course of nucleic acid amplification reaction.

The bulge in the DNA fragment in accordance with the present invention is preferably a cytosine bulge for the following reasons. 2,7-Diamino-1,8-naphthyridine (detailed later) is a fluorescent substance, and when bound to a cytosine bulge, shifts its local absorption maximum wavelength for fluorescence and fluoresces with higher intensity at the post-shifting wavelength. Therefore, the use of 2,7-diamino-1,8-naphthyridine enables a specific and high sensitivity detection of nucleic acid amplification.

The cytosine bulge in the DNA fragment in accordance with the present invention may be formed from any base sequence provided that the cytosine bulge can be formed from the base sequence. Preferably, the two Ts in the TCT sequence and the two As in the AA sequence in the single-stranded DNA fragment are paired in the DNA fragment molecules (intramolecular pairing) by T-A base pairs, and the C between the two Ts acts as the bulge base in forming the cytosine bulge. This design is preferred because the hairpin structure containing a cytosine bulge formed by the T-A base pairs between the TCT and AA sequences in the DNA is stable and enables desirable binding of bulge-binding molecules. At the same time, the hairpin structure is not excessively stable and allows for desirable linearization of the hairpin structure in nucleic acid amplification reaction. Another reason is that if the compound containing a naphthyridine ring (detailed later) is used, the resultant fluorescence shifts toward longer wavelengths where measurement sensitivity improves.

Concrete Examples of Base Sequence in DNA Fragment in Accordance with the Present Invention The base sequences according to SEQ ID NOs 1 to 5 are some concrete examples of the base sequence in the DNA fragment in accordance with the present invention explained above. Among them, the base sequences according to SEQ ID NOs 1 to 4 are preferred because the cytosine bulge is formed by the pairing of the TCT and AA sequences in the DNA. The base sequences according to SEQ ID NOs 1 to 3 are more preferred because they form plural cytosine bulges.

Hairpin Primer in Accordance with the Present Invention

The "hairpin primer," throughout this specification, is intended to mean a primer used in nucleic acid amplification reaction having a 5' end to which is attached the DNA fragment in accordance with the present invention.

The hairpin primer in accordance with the present invention only needs to be a primer designed for use in nucleic acid amplification reaction for amplification of target nucleic acid and having a 5' end to which is attached the DNA fragment in accordance with the present invention.

In other words, the hairpin primer in accordance with the present invention is obtainable by designing a primer for use in nucleic acid amplification reaction by a publicly known design technique and attaching the DNA fragment in accordance with the present invention to the 5' end of the primer.

The DNA fragment in accordance with the present invention is attached to the primer used in nucleic acid amplification reaction by, for example, using a publicly known DNA ligase. Alternatively, the hairpin primer in accordance with the present invention is obtainable by carrying out continuous chemical synthesis on a base sequence containing both the primer used in nucleic acid amplification reaction and the DNA fragment in accordance with the present invention already attached to the primer.

The hairpin primer in accordance with the present invention is suitable for use in various nucleic acid amplification reactions: e.g., PCR (Nested-PCR, reverse transcription PCR, hot start PCR, and TaqMan PCR), ICAN, UCAN, and LAMP. The hairpin primer is especially suitable for use in PCR. Employing the hairpin primer in accordance with the present invention in PCR, which is a convenient technique for nucleic acid amplification reactions, provides a quick and convenient tool to implement procedures from amplification of a target nucleic acid to the confirmation of the amplification.

Nucleic Acid Amplification Confirmation Method in Accordance with the Present Invention The nucleic acid amplification confirmation method in accordance with the present invention only needs to involve: the step of preparing a nucleic acid amplification reaction liquid containing a set of primers at least one of which is the hairpin primer in accordance with the present invention; the unreacted hairpin primer measuring step of quantifying the hairpin primer in the nucleic acid amplification reaction liquid using bulge-binding molecules; the step of carrying out the nucleic acid amplification reaction; and the reacted hairpin primer measuring step of, after the nucleic acid amplification reaction is terminated, quantifying the hairpin primer in the nucleic acid amplification reaction liquid using bulge-binding molecules.

The nucleic acid amplification reaction linearizes the bulge(s) in the hairpin primer in accordance with the present invention. Therefore, by using bulge-binding molecules, the quantity of the bulge(s), hence the quantity of the hairpin primer, in the reaction liquid can be compared over the course of nucleic acid amplification reaction. Specifically, amplification of a nucleic acid is confirmed if the quantity of the hairpin primer decreases over the amplification. If not, failure of amplification of the nucleic acid is confirmed.

The following will describe an embodiment of the nucleic acid amplification confirmation method in accordance with the present invention in reference to FIG. 1.

FIG. 1 is a schematic drawing illustrating the basic mechanism of the nucleic acid amplification confirmation method according to the present embodiment. In FIG. 1, PCR is employed as the nucleic acid amplification reaction.

The line segment at the bottom in (1) of FIG. 1 represents DNA containing a target nucleic acid to be amplified. In other words, (1) of FIG. 1 illustrates a hairpin primer in accordance with the present invention being annealed to the nucleic acid to be analyzed. The primer is capable of amplifying the nucleic acid and attached at the 5' end to a DNA fragment in accordance with the present invention containing a hairpin structure containing a cytosine bulge. A complementary chain is synthesized by extension reaction in the direction indicated by a broken line.

Next, referring to (2) of FIG. 1, a reverse primer is annealed to the DNA chain synthesized in (1) of FIG. 1, and a DNA chain is synthesized, extending in the direction indicated by a broken line, that is, opposite to the direction in (1) of FIG. 1.

The progress of PCR as in (1) and (2) of FIG. 1 linearizes the hairpin structure which is formed by the forward hairpin primer as illustrated in (3) of FIG. 1. The bulge in the hairpin structure thus disappears.

(4) of FIG. 1 illustrates a bulge-binding fluorescent molecule 1 added to a reaction liquid after the hairpin primer is annealed to the nucleic acid to be amplified as in (1) of FIG. 1. In other words, the bulge-binding fluorescent molecule 1 binds to the cytosine bulge and fluoresces at the post-shifting local absorption maximum wavelength. Details will be given later about the bulge-binding fluorescent molecule. Briefly, the bulge-binding fluorescent molecule 1 is used in the present embodiment can be described as a fluorescent substance of which the local absorption maximum wavelength for fluorescence shifts when bound to a bulge.

(5) of FIG. 1 illustrates the bulge-binding fluorescent molecule 1 added to the reaction liquid after the PCR is terminated. The bulge-binding fluorescent molecule 1 cannot bind to the amplified nucleic acid because the original hairpin primer had its hairpin structure linearized in the PCR and lost the bulge. Therefore, the fluorescence intensity is very low.

The hairpin primer in accordance with the present invention is quantified before and after the PCR in this way. If the measurement decreases, it is confirmed that the target nucleic acid region has been amplified.

The nucleic acid amplification reaction may be performed by a publicly known method using publicly known apparatus. Suitable reaction conditions are determined based on the samples and primers used and other factors.

The samples to which the nucleic acid amplification confirmation method in accordance with the present invention is applicable only need to contain nucleic acid, and are otherwise not limited in any particular manner. Examples include body fluids, such as blood, lymph, nasal discharge, expectoration, urine, faeces, and ascitic fluid; tissues, such as skin, mucous membrane, various internal organs, and bones; washings in which nasal cavity, bronchi, skin, various internal organs, and bones were cleaned; vegetables; and microorganisms.

Any nucleic acid, either DNA or RNA, derived from these samples may be used. The DNA may be genome DNA, cDNA, etc. The RNA may be mRNA, rRNA, tRNA, etc. If RNA is used, the method preferably includes a step for synthesizing DNA by reverse transcription reaction.

Detection of Bulges

The unreacted hairpin primer measuring step and the reacted hairpin primer measuring step are performed by detecting bulges after binding bulge-binding molecules to the bulges of the hairpin primers in accordance with the present invention.

The bulge-binding molecules used in the nucleic acid amplification confirmation method in accordance with the present invention are by no means limited provided that they can bind to bulges. Preferably, the molecules are a fluorescent substance and when bound to bulges, come to fluoresce, shift its fluorescence wavelength, stop fluorescing, or otherwise change their fluorescence so that the bulges can be readily detected by detecting these changes in the fluorescence. Non-fluorescent bulge-binding molecules may be used, in which case the bulge-binding molecules are labelled separately with a fluorescent substance or charged in an affinity chromatography column when used.

An example of a bulge-binding molecule that changes its fluorescence emission when bound to a bulge is a compound containing a naphthyridine ring. When bound to an adenine bulge or a guanine bulge, naphthyridine ring-containing compounds no longer fluoresce. In addition, the compound, when bound to a cytosine bulge or a thymine bulge, shifts its local absorption maximum wavelength for fluorescence. Bulges can be detected conveniently through the detection of the lack of fluorescence or the fluorescence at the post-shifting local absorption maximum wavelength.

The naphthyridine ring-containing compound does not disrupt activities of the enzymes used in the nucleic acid amplification reaction (e.g. DNA polymerase). The samples can be subjected to the nucleic acid amplification reaction without having to remove the naphthyridine ring-containing compound. Therefore, changes in fluorescence can be evaluated by: preparing a nucleic acid amplification reaction liquid, mixing the liquid with a naphthyridine ring-containing compound in advance in a single reaction container, then measuring the fluorescence of the reaction liquid, subjecting the reaction liquid in this condition to the nucleic acid amplification reaction, and after the amplification reaction is terminated, measuring again the fluorescence of the reaction liquid.

The use of a naphthyridine ring-containing compound as the bulge-binding molecules hence enables convenient confirmation of nucleic acid amplification in the nucleic acid amplification reaction (hereinafter, the "naphthyridine ring-containing compound" will be referred to as the "bulge-binding fluorescent molecule(s)").

The bulge-binding fluorescent molecule used in the nucleic acid amplification confirmation method in accordance with the present invention is preferably a 2,7-diamino naphthyridine derivative of chemical formula 1:

Chem. 3

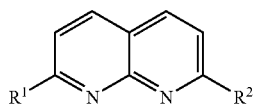

(1)

where each of $R^1$ and $R^2$, mutually independent, is a primary amine residue, a secondary amine residue, or a tertiary amine residue. The primary amine residue is, for example, —$NH_2$. The secondary amine residue is, for example, an —$NH(CH_2)NH_2$ group, an —$NH(CH_2)_2NH_2$ group, or an —$NH(CH)_2NH(CH_3)$ group. The tertiary amine residue is, for example, an —$N(CH_3)(CH_2)_2NH_2$ group. Preferably, at least either one of $R^1$ and $R^2$ is a secondary amine residue. More preferably, both $R^1$ and $R^2$ are a secondary amine residue. The presence of the secondary amine residue(s) in the bulge-binding fluorescent molecule stabilizes the binding with the bulge.

Among the 2,7-diamino naphthyridine derivatives, 2,7-diamino-1,8-naphthyridine of chemical formula 2 is especially preferred.

Chem. 4

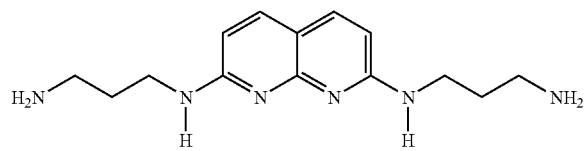

(2)

2,7-Diamino-1,8-naphthyridine, when bound to a cytosine bulge, shifts its local absorption maximum wavelength for fluorescence and emits fluoresce with high intensity at that post-shifting wavelength. Cytosine bulges, hence the hairpin primer in accordance with the present invention used in nucleic acid amplification reaction, can be specifically detected with high sensitivity.

2,7-Diamino-1,8-naphthyridine can be synthesized by a publicly known method. e.g., the method described in Japanese Patent Application Publication, Tokukai, No. 2004-262827. A local absorption maximum is detected at 376 nm when 2,7-diamino-1,8-naphthyridine is alone in a 10 mM buffer solution of sodium phosphate (pH=7.0). The maximum shifts to 396 nm when the 2,7-diamino-1,8-naphthyridine is bound to cytosine bulges.

The bulge-binding fluorescent molecule of chemical formula 1 may be a 2,7-diamino-1,8-naphthyridine derivative of chemical formula 3 or chemical formula 4:

Chem. 5

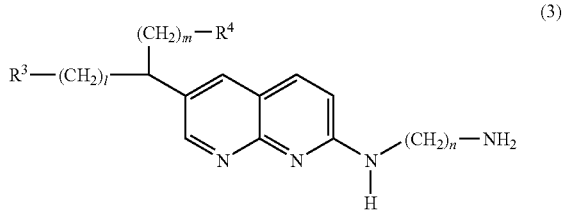

(3)

where each of $R^3$ and $R^4$, mutually independent, is either a hydrogen atom or an amino group, and each of l, m, and n, mutually independent, denotes a natural number from 1 to 6; and Chem. 6

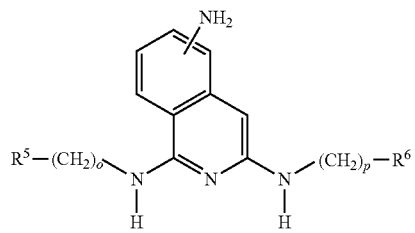

(4)

where each of $R^5$ and $R^6$, mutually independent, is either a hydrogen atom or an amino group, and each of o and p, mutually independent, denotes a natural number from 1 to 6.

The pH in detecting the hairpin primer in accordance with the present invention by using the bulge-binding fluorescent molecule is preferably 5 or higher, more preferably 6 or higher, and even more preferably 6.5 or higher. The pH does not exceed preferably 9, more preferably 8, and even more preferably 7.5. If the pH is from 5 to 9, inclusive, DNA is stable and the bulge-binding fluorescent molecule binds to the bulge of the hairpin primer in accordance with the present invention in a satisfactory manner. Accordingly, fluorescence is detected in a satisfactory manner.

The bulge-binding fluorescent molecule may be added directly to the reaction liquid used in the nucleic acid amplification reaction. A buffer solution of phosphoric acid or Tris-HCL may also be used, for example.

The bulge-binding fluorescent molecule is used in an amount of preferably 20 moles to 100 moles, and more preferably 40 moles to 60 moles, per every mole of the hairpin primer added in advance to the reaction liquid for the nucleic acid amplification reaction. If the amount is from 20 moles to 100 moles, there are sufficient molecules binding to the bulges in the hairpin primer, and the background signal is low and causes no measurement errors or other inconveniences.

The detection of fluorescence of the bulge-binding fluorescent molecules when they bind to the bulges is by no means limited provided the fluorescence is detectable. The wavelength is preferably 400 nm to 480 nm, and more preferably 430 to 460 nm. The fluorescence at 400 nm to 480 nm has sufficient intensity to discriminate clearly against the fluorescence of 2,7-diamino-1,8-naphthyridine bound to no bulges.

The fluorescence intensity detailed above can be detected by a publicly known method using publicly known apparatus (for example, a conventional fluorescence plate reader).

SNP Detection Method

The SNP detection method in accordance with the present invention involves the nucleic acid amplification confirmation method in accordance with the present invention.

The nucleic acid amplification confirmation method in accordance with the present invention is employed in the nucleic acid amplification reaction for which amplification conditions are set so that the nucleic acid may or may not be amplified by the nucleic acid amplification reaction depending on the type of the base at the target SNP site. The approach enables quick, convenient, inexpensive, and highly sensitive detection of base types at the SNP site in nucleic acid.

The primers used in the SNP detection method in accordance with the present invention are by no means limited provided that the primers are designed so that the nucleic acid may or may not be amplified depending on the type of the base at the target SNP site in the nucleic acid. Preferably, any one of primers in the above set of primers is designed to have a 3' end located where the detection target SNP is located.

It largely affects the progress of the nucleic acid amplification reaction whether or not a normal base pair can be formed by the base located at the 3' end of the primer and the nucleic acid used in the nucleic acid amplification reaction. Accordingly, by designing any one of primers in the set of primers to have a 3' end located where the detection target SNP is located, one can readily find such amplification conditions that the nucleic acid may or may not be amplified depending on the type of the base at the SNP site.

A suitable base type in view of the objectives of the SNP detection and the target base at the SNP site may be selected for the 3' end of the primer which is, for use in the SNP detection method in accordance with the present invention, designed to have its 3' end located where the detection target SNP is located.

For example, to find out whether the base at the SNP site is a particular type of base or replaced by another type (mutation), one only needs to locate at the 3' end a base complementary to that particular base. If the nucleic acid is amplified, the base at the SNP site is determined to be of the particular type; if the nucleic acid is not amplified, the base at the SNP site is determined to have been replaced by a different type of base (mutation).

Moreover, if the base type at the SNP site is predictable, the reliability of results of the detection is improved by preparing primers each having at the 3' end a base complementary to a different possible type and performing the nucleic acid amplification reaction using the primers. The nucleic acid is amplified in the nucleic acid amplification reaction using one of the primers and not amplified in the nucleic acid amplification reactions using the other primers. The base type at the SNP site is hence more reliably determined.

Figure 2:
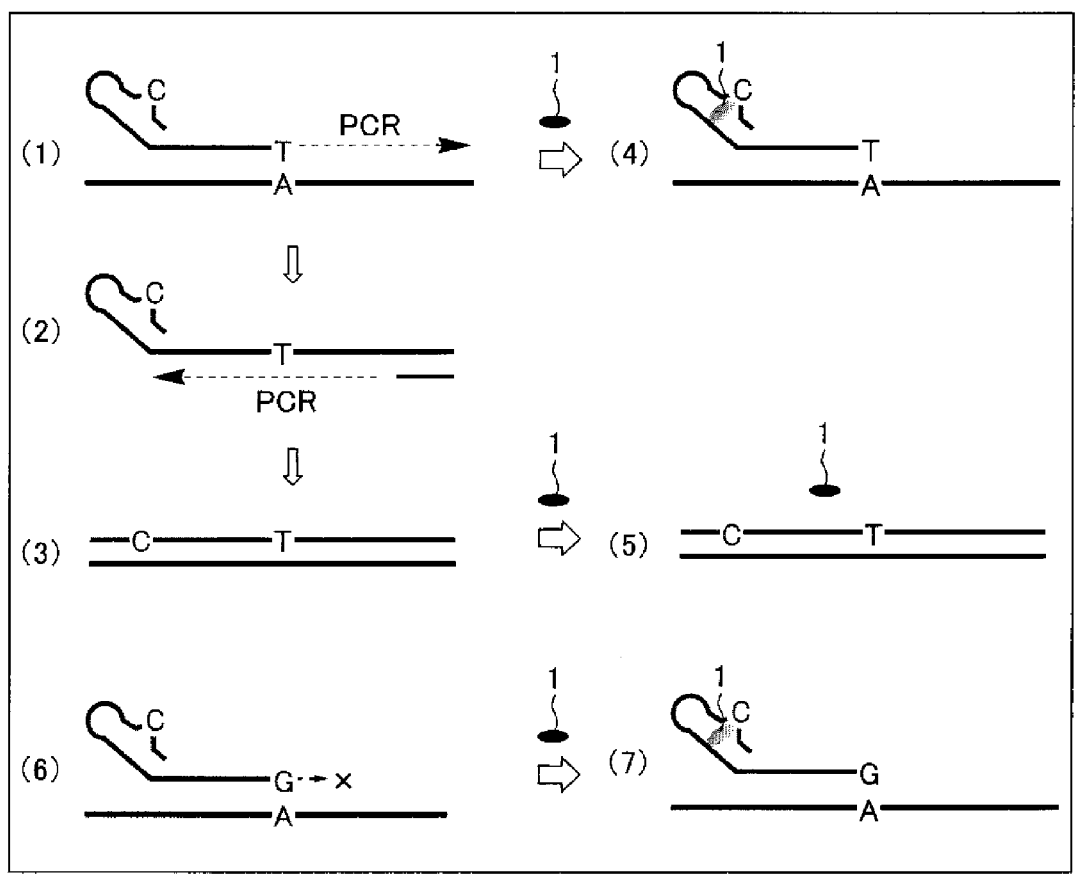

The following will describe an embodiment of the SNP detection method in accordance with the present invention in reference to FIG. 2.

FIG. 2 is a schematic drawing illustrating a basic mechanism of the SNP detection method of the present embodiment. PCR is employed as the nucleic acid amplification reaction in FIG. 2.

The straight line containing A (adenine) in (1) of FIG. 2 represents a nucleic acid to be analyzed which has an SNP where the A (adenine) is located. In other words, (1) of FIG. 2 illustrates a hairpin primer in accordance with the present invention being annealed to the nucleic acid to be analyzed. The hairpin primer contains a primer and a DNA fragment in accordance with the present invention containing a hairpin structure containing a cytosine bulge. The primer contains at the 3' end a T (thymine), which is a base complementary to the A (adenine), and is attached at the 5' end to the DNA fragment. A complementary chain is synthesized by extension reaction, extending in the direction indicated by a broken line.

Next, referring to (2) of FIG. 2, a reverse primer is annealed to the DNA chain synthesized in (1) of FIG. 2, and a DNA chain is synthesized extending in the direction indicated by a broken line, that is, opposite to the direction in (1) of FIG. 2. The reverse primer used here only needs to be designed downstream of the SNP site.

The progress of PCR as in (1) and (2) of FIG. 2 linearizes the hairpin structure which is formed by the forward hairpin primer as illustrated in (3) of FIG. 2. The bulge in the hairpin structure thus disappears.

(4) of FIG. 2 illustrates a bulge-binding fluorescent molecule 1 added to a reaction liquid after the hairpin primer is annealed to the nucleic acid to be analyzed as in (1) of FIG. 2. In other words, the bulge-binding fluorescent molecule 1 binds to the cytosine bulge and fluoresces at the post-shifting local absorption maximum wavelength.

(5) of FIG. 2 illustrates the bulge-binding fluorescent molecule 1 added to the reaction liquid after the PCR is terminated. The bulge-binding fluorescent molecule 1 cannot bind to the amplified nucleic acid because the original hairpin primer had its hairpin structure linearized in the PCR and lost the bulge. Therefore, the fluorescence intensity is very low.

The base at the SNP site of the nucleic acid to be analyzed is hence determined to be an A (adenine).

(6) of FIG. 2 illustrates the same nucleic acid as in (1) being subjected to PCR for analysis. In the PCR, a hairpin primer in accordance with the present invention is used as a forward primer. The hairpin primer contains a G (guanine) at the 3' end and is attached at the 5' end to a DNA fragment in accordance with the present invention containing a hairpin structure containing a cytosine bulge. The hairpin primer is designed to contain the G (guanine) so that the PCR proceeds if the nucleic acid to be analyzed contains an SNP and the base at the SNP site is a C (cytosine).

The base at the SNP site of the nucleic acid subjected to the PCR is, however, an A (adenine), not a C (cytosine) in (6) of FIG. 2. Therefore, the PCR does not proceed. A large quantity of unreacted hairpin primers containing a cytosine bulge remains in the post-PCR reaction liquid.

(7) of FIG. 2 illustrates the state after the PCR is carried out as in (6) of FIG. 2. The hairpin primers in accordance with the present invention remain unreacted because the PCR did not proceed in (6) of FIG. 2 as mentioned above. The bulge-binding fluorescent molecule 1 in the reaction liquid therefore binds to the cytosine bulge in the hairpin primer and fluoresces at the post-shifting local absorption maximum wavelength. Therefore, the fluorescence intensity of the bulge-binding fluorescent molecule 1 at the wavelength hardly changes over the course of the PCR shown in (6) of FIG. 2. The fluorescence intensity at the wavelength is greater in (7) of FIG. 2 than in (5) of FIG. 2.

Accordingly, the base at the SNP site of the nucleic acid to be analyzed is determined not to be a C (cytosine).

The hairpin primer in accordance with the present invention is used in this manner in the nucleic acid amplification reaction for which amplification conditions are set so that the nucleic acid may or may not be amplified depending on whether or not the target nucleic acid contains an SNP or another mutation as in allele specific PCR. The approach enables quick, convenient, inexpensive, and highly sensitive detection of the presence/absence of a mutation in the nucleic acid.

Competitor Primer

The SNP detection method in accordance with the present invention only requires the use of a hairpin primer as the primer designed to have a 3' end located where the detection target SNP is located. Preferably, the nucleic acid amplification reaction liquid contains a competitor primer designed to have a 3' end located where the detection target SNP is located and to contain at the 3' end a base complementary to the base in a mutated nucleic acid where the target SNP is to be detected if the hairpin primer is used to amplify a wildtype nucleic acid and a base complementary to the base in a wildtype nucleic acid where the target SNP is to be detected if the hairpin primer is used to amplify a mutated nucleic acid.

Accordingly, for example, when a hairpin primer is used to amplify a wildtype nucleic acid, the competitor primer containing at its 3' end a base complementary to the base in a mutated nucleic acid where the target SNP is to be detected is more likely to be annealed to the mutated nucleic acid, preventing the hairpin primer from being annealed to the mutated nucleic acid. The hairpin primer intended to amplify a wildtype nucleic acid is prevented from being used up to amplify a mutated nucleic acid. The approach prevents mistaking amplification of the mutated nucleic acid for amplification of the wildtype nucleic acid. Therefore, the reliability of results of the SNP detection is improved.

In addition, for example, when a hairpin primer is used to amplify a mutated nucleic acid, the competitor primer containing at its 3' end a base complementary to the base in a wildtype nucleic acid where the target SNP is to be detected is more likely to be annealed to the wildtype nucleic acid, preventing mistaking amplification of the wildtype nucleic acid for amplification of the mutated nucleic acid similarly to the cases where a hairpin primer is used to amplify a wildtype nucleic acid. Therefore, the reliability of results of the SNP detection is improved.

The "competitor primer" throughout this specification refers to the primer that is more likely to be annealed to a non-target nucleic acid in amplification confirmation than another primer which, if used in the nucleic acid amplification reaction, could also be annealed to the non target nucleic acid.

The "wildtype nucleic acid" throughout this specification refers to the nucleic acid containing the base that frequently appears where the target SNP is located. The "mutated nucleic acid" refers to the nucleic acid containing the base that infrequently appears where the target SNP is located.

The competitor primer used in the SNP detection method in accordance with the present invention is designed to contain such a base sequence that the base at the 3' end is, if the hairpin primer is used to amplify a wildtype nucleic acid, a base complementary to the base at an SNP site in a mutated nucleic acid and if the hairpin primer is used to amplify a mutated nucleic acid, a base complementary to the base at an SNP site in a wildtype nucleic acid.

For example, the hairpin primer in (6) of FIG. 2, if designed to remove the hairpin structure and substitute T (complementary to A) at the 3' end, can be used as a competitor primer in the PCR in (6) of FIG. 2. The competitor primer is more likely to be annealed to the nucleic acid subjected to the PCR in (6) of FIG. 2 than the hairpin primer. The competitor primer hence prevents the PCR from proceeding with part of the hairpin primer in (6) of FIG. 2 being annealed to the nucleic acid containing A, which is a non-target base in the detection, in (6) of FIG. 2. Otherwise, the particular annealing could be a cause for mistaking the base at the SNP site for being a C.

In real time PCR, fluorescence is detected even if a non target nucleic acid is amplified. Reliable results are not expected if real time PCR is used in SNP detection without any modifications. To improve reliability, for example, a fluorescent-labelled probe should be used which specifically hybridizes to the base type at the SNP site. These additional procedures add to complexity of the operation.

In contrast, the SNP detection method in accordance with the present invention, if used in conjunction with a competitor primer, is capable of preventing the hairpin primer from being consumed in the amplification of a mutated nucleic acid in which a non-target base is present at the SNP site. The method thus increases the reliability of results of confirmation of nucleic acid amplification, enabling more convenient SNP detection with higher reliability than real time PCR.

The use of a competitor primer prevents the hairpin primer in accordance with the present invention from being annealed to a nucleic acid which is not targeted in the confirmation of amplification, not only in SNP detection, but also in PCR and like nucleic acid amplification reactions. In other words, the use prevents the amplification of the non-target nucleic acid from being mistaken for the amplification of the target nucleic acid.

In this case, the competitor primer is designed with such a base sequence that the competitor primer can be annealed to a region containing a region in the non-target nucleic acid to which the hairpin primer in accordance with the present invention could be annealed and also that the region of the competitor primer where it is annealed to the non-target nucleic acid can be more homologous to the non-target nucleic acid than is the hairpin primer. It is noted that the base sequence in the region to which the hairpin primer could be annealed must be known.

Accordingly, the hairpin primer in accordance with the present invention is prevented from being consumed by the nucleic acid which is not targeted in the confirmation of amplification. In other words, the fluorescence intensity explained above of the bulge-binding fluorescent molecule is prevented from decreasing due to non-intended nucleic acid amplification reaction. Also, the specificity of the confirmation of amplification is improved.

Reagent Kit in Accordance with the Present Invention

The reagent kit in accordance with the present invention only needs to contain at least the DNA fragment in accordance with the present invention. Additionally, the kit may contain a DNA ligase or like reagent which attaches the DNA fragment in accordance with the present invention to the 5' end of a nucleic acid amplification primer designed freely by users of the kit.

Furthermore, the reagent kit in accordance with the present invention may contain the hairpin primer in accordance with the present invention with which a particular SNP can be detected based on available SNP information. The kit may also contain the bulge-binding molecule, bulge-binding fluorescent molecule, or competitor primer described above.

The kit may be arranged otherwise. It may contain other reagents and tools: e.g. reagents and tools for PCR (DNA polymerase, dNTP, a PCR buffer, PCR tubes, etc.), amplified nucleic acid purification reagents and tools, reagents and buffer solutions for stable preservation of DNA fragments, and reagents and buffer solutions for stable preservation of bulge-binding molecules and bulge-binding fluorescent molecules.

Any of the above arrangements includes a preferable agent or an equivalent to confirm nucleic acid amplification in nucleic acid amplification reaction. The use of the reagent kit in accordance with the present invention therefore enables easy and quick confirmation of nucleic acid amplification in nucleic acid amplification reaction, establishing a way to exploit the present invention in the clinical test, pharmaceutical, and other industrial level applications.

The reagent kit in accordance with the present invention may be provided in the form of various products. An example product would include DNA fragments in accordance with the present invention, bulge-binding fluorescent molecules, and other miscellaneous reagents either in a single container of a suitable capacity and/or form or in individual containers. The reagent kit in accordance with the present invention may additionally include a manual which explains procedures to confirm nucleic acid amplification in nucleic acid amplification reaction.

The present invention is not limited to the description of the embodiments above, but may be altered by a skilled person within the scope of the claims. An embodiment based on a proper combination of technical means disclosed in different embodiments is encompassed in the technical scope of the present invention.

Cost Advantage of the Present Invention

The present invention provides a low cost means of carrying out the above SNP analysis and like processes in comparison with conventional methods.

The following description will elaborate on this particular point by comparison of the SNP analysis by means of PCR using the hairpin primer in accordance with the present invention and conventional SNP analysis (Invader assay). The following Invader assay was conducted based on description in "The Invader assay for SNP genotyping," M. Olivier, 2005, Mutation Research, 573, 103-110.

First, Table 1 shows major reagents in PCR used along with the hairpin primer in accordance with the present invention and in conventional Invader assay.

TABLE 1

|  | Types of Oligomer | Chemical Modification of Oligomer | Other Major Reagents |
| --- | --- | --- | --- |
| Present Invention | 2 or 3 | Not Required | DNA polymerase, Bulge-binding Fluorescent Molecule |
| Invader assay | 3 or 5 | Required | Flap Endnuclease |

Table 2 shows results of a qualitative comparison of cost in relation to the reagents in Table 1. In Table 2, a cross indicates that the cost is extremely high, a triangle indicates that the cost is high, a circle indicates that the cost is low, and a double circle indicates that the cost is extremely low.

TABLE 2

|  | Oligomer | Chemical Modification of Oligomer | Other Major Reagents | Overall Cost |
| --- | --- | --- | --- | --- |
| Present Invention | ○ | ◎ (Not Required) | Δ | ○ |
| Invader Assay | X | X | ○ | X |

As shown in Tables 1 and 2, the PCR using the hairpin primer in accordance with the present invention requires fewer oligomers, hence less costly in this regard, than conventional Invader assay.

The PCR using the hairpin primer in accordance with the present invention requires only 2 or 3 types of oligomers. As an example, if the hairpin primer in accordance with the present invention is used as the forward primer, and a separately fabricated reverse primer is used, the PCR can be conducted, in which case only 2 types of oligomers are needed. For a comparative study of a case where nucleic acid amplification occurs and a case where the amplification does not occur, as illustrated in FIG. 2, the base at the 3' end of the hairpin primer in accordance with the present invention is replaced with a different base. The sequence of the reverse primer however does not need to be changed. Therefore, the study requires 3 types of oligomers: 2 types of hairpin primers in accordance with the present invention with different 3' end bases and a single type of primer.

Meanwhile, conventional Invader assay requires at least 3 types of oligomers: Invader oligo, primary probe, and FRET cassette. A comparative study of a case where nucleic acid amplification occurs and a case where the amplification does not occur requires another type of primary probe and another type of FRET cassette. That means the study requires in total 5 types of oligomers.

The PCR using the hairpin primer in accordance with the present invention is advantageous over the conventional method in that fewer oligomers are needed.

Furthermore, as shown in Tables 1 and 2, chemical modifications of the oligomer are not needed in the hairpin primer in accordance with the present invention, whilst they are essential in the conventional Invader assay. The difference makes the PCR using the hairpin primer in accordance with the present invention far less costly than the conventional Invader assay.

Specifically, the conventional Invader assay requires chemical modification of the FRET cassette at two sites, one with a fluorescence pigment and the other with a quencher. The chemical modifications are extremely costly.

If the hairpin primer in accordance with the present invention used as an non-oligomer reagent, DNA polymerase and bulge-binding fluorescent molecules are needed as shown in Tables 1 and 2. Meanwhile, a flap endonuclease may be used as an enzyme in the conventional Invader assay. The cost of the DNA polymerase, however, is more or less the same as the cost of the flap endonuclease, and the bulge-binding fluorescent molecules are extremely cheap. Therefore, if the hairpin primer in accordance with the present invention is used as the non-oligomer reagent, the present invention costs only slightly more than the conventional Invader assay.

2,7-Diamino-1,8-naphthyridine (used in an example below) and many other bulge-binding fluorescent molecules can be manufactured from 2,6-diamino pyridine and DL-malic acid. Both of them, available from Tokyo Chemical Industry Co., Ltd., are inexpensive at 5,900 Japanese yen per every 25 grams and 2,200 Japanese yen per every 500 grams, respectively. A 90% discount will be given for large volume purchase. Apart from these materials, 1,3-diamino propane and phosphorous oxychloride are used in some cases. The former is inexpensive at 5400 Japanese yen per every 500 mL. The latter is available at a very low price as an industrial material. Besides, a single round of PCR needs as little as about 50 μmol/L of the bulge-binding fluorescent molecules. The cost of the bulge-binding fluorescent molecules is extremely low (almost negligible) in the overall cost when compared with the cost of the oligomers used.

The above evaluation, when considered as a whole, demonstrates that the present invention is capable of implementing the above SNP analysis and like processes at extremely low cost than the conventional method.

EXAMPLES

The invention will be described by way of examples of PCR using the DNA fragment in accordance with the present invention together with bulge-binding fluorescent molecules.

The hairpin primers shown in FIG. 3 were used in the following examples. FIG. 3 gives the name of each hairpin primer used in the examples along with a schematic illustration of its base sequence and structure. The primers identified as takei 5, takei 18, takei 18-4, takei 2, and takei 2-2 were hairpin primers formed by the DNAs containing base sequences according to SEQ ID NOs 6 to 10, respectively. Specifically, they contained the same base sequence as the one according to SEQ ID NO 11 and was attached at its 5' end to the DNA containing the base sequences according to SEQ ID NOs 1 to 5 respectively.

In FIG. 3, "A_A" denotes AA, or a sequence of two consecutive As. These As paired respectively with the Ts in the TCT located opposite to the As. The As are separated by "_" because the base which could have paired with the C was missing. Similarly, the Ts in "T_T" are separated by "_" because the two Ts paired respectively with the As located opposite to the Ts, and the base which could have paired with the C between the two As was missing. All the hairpin primers in FIG. 3 contained a cytosine bulge.

Example 1

In this example, pUC 18 (GenBank Accession Number L09136), which was a publicly known plasmid, was used as a sample DNA and as a template in PCR under the following conditions.

In the PCR of the present example, takei 5 was used as the reverse primer, and the DNA having the base sequence according to SEQ ID NO 12 was used as the forward primer (hereinafter, the primer will be referred to as "M13M3").

The PCR reaction liquid was 50 μL in total and contained 5 ng of pUC 18, 0.5 μM of the forward primer, 0.5 μM of the reverse primer, and 25 μL of the Taq DNA polymerase which came in a Taq PCR Master Mix Kit package (manufactured by QIAGEN), with the balance being water. To the PCR reaction liquid was added 20 μM of 2,7-diamino-1,8-naphthyridine ("DANP") of chemical formula 2 as the bulge-binding fluorescent molecule.

Temperature conditions for the PCR were 40 cycles of 98° C. for 10 seconds, 55° C. for 30 seconds, and 72° C. for 30 seconds, followed by 4° C. during storage.

Fluorescence intensity was detected with excitation wavelength of 400 nm and with fluorescence detection wavelength of 450 nm using a fluorescence plate reader (Mithras LB940 manufactured by Berthold Technologies).

Next, the fluorescence intensity of the PCR reaction liquid before the PCR was measured. The PCR reaction liquid was then subjected directly to the PCR. The fluorescence intensity of the reaction liquid was measured after the PCR was terminated.

Figure 4:
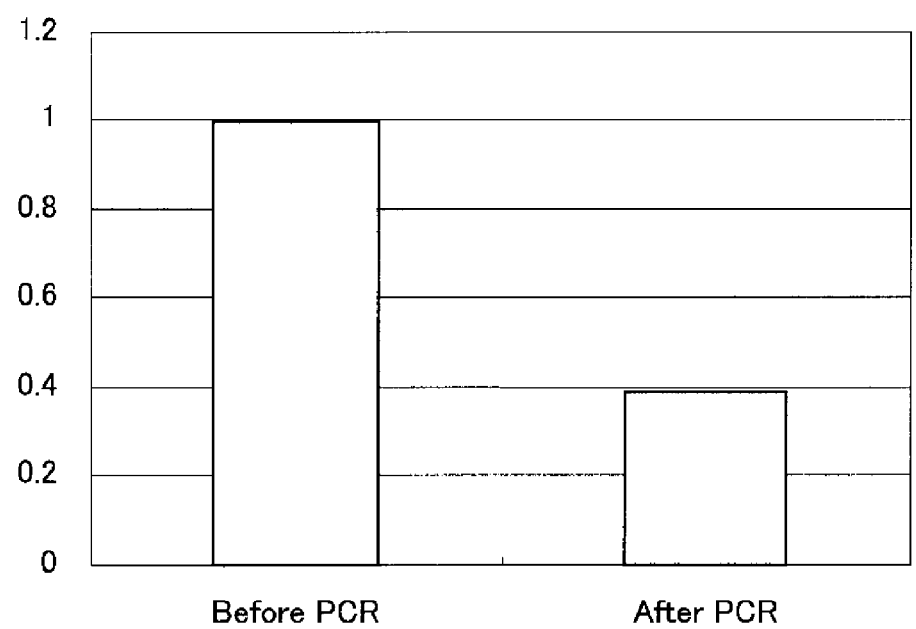

A comparison of the fluorescence intensity before and after the PCR is shown in FIG. 4 and Table 3.

TABLE 3

| | Before PCR | After PCR |
|---|---|---|
| Fluorescence Intensity | 1 | 0.39 |

FIG. 4 shows a comparison of the pre-PCR and post-PCR fluorescence intensity.

As can be appreciated from Table 3 and FIG. 4, the fluorescence intensity of the reaction liquid decreased by about 40% over the course of the PCR, an indication that the PCR had taken place and nucleic acid had been amplified.

Example 2

In this example, it was examined by using takei 2 and takei 2-2 how the fluorescence intensity of the bulge-binding fluorescent molecule varied with the base sequences forming the cytosine bulge.

The reaction liquid used in the example was 400 μL in total and contained 50 μM of DANP, 0.01 M of phosphoric acid, 0.1 M of NaCl, and 5 μM of either takei 2 or takei 2-2, with the balance being water.

The fluorescence intensity was measured with a fluorescence measuring instrument (Shimadzu Corporation, RF-5300PC), and fluorescence detection wavelength was changed from 350 nm to 600 nm. Results are shown in FIG. 5.

Figure 5:
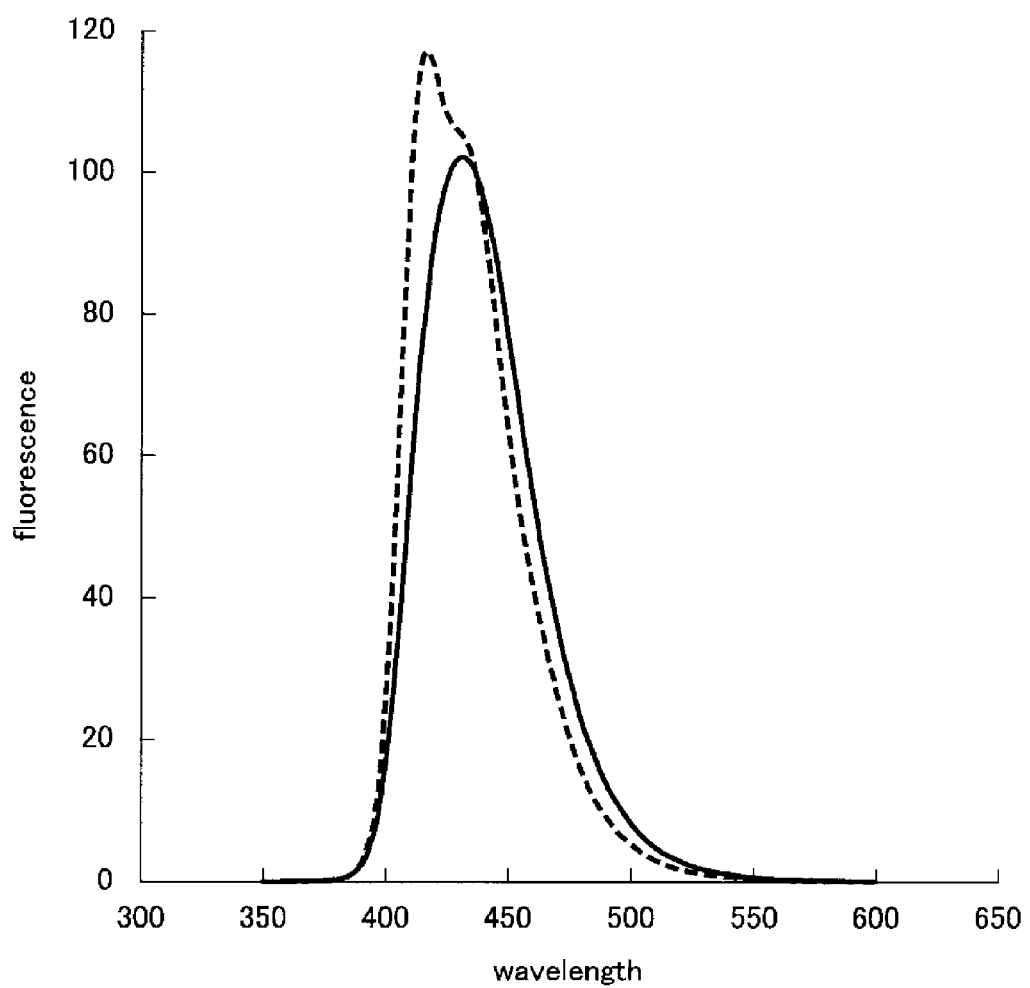

FIG. 5 shows fluorescence intensity on the vertical axis and fluorescence detection wavelength on the horizontal axis. The solid line was obtained by plotting results from takei 2, and the broken line from takei 2-2. As can be appreciated from FIG. 5, the fluorescence wavelength shifted toward longer wavelengths when takei 2 was used, that is, when the cytosine bulge was formed by AA-TCT binding. These results show that when takei 2 was used, the shift from the fluorescence intensity of non-bulge binding DANP to the fluorescence intensity of bulge-binding DANP was greater. The results demonstrate that the cytosine bulge, if formed by AA and TCT binding, enables high sensitivity measurement, hence high sensitivity PCR amplification confirmation.

Example 3

It was examined in this example how PCR cycles are related to the fluorescence intensity of the bulge-binding fluorescent molecule.

Takei 5 and takei 18 were used as the reverse primer, and M13M3 was used as the forward primer, in the example.

The PCR reaction liquid was 300 μL in total and contained 30 ng of pUC is, 0.5 μM of the forward primer, 0.5 μM of the reverse primer, and 150 μL of the Taq DNA polymerase which came in a Taq PCR Master Mix Kit package (manufactured by QIAGEN), with the balance being water. Furthermore, 20 μM of DANP was added as the bulge-binding fluorescent molecule.

The PCR was carried out at 98° C. for 10 seconds, 55° C. for 30 seconds, and 72° C. for 30 seconds. The fluorescence intensity of the PCR reaction liquid was measured before performing the PCR on the liquid. The PCR reaction liquid was then subjected directly to the PCR. Thereafter, the fluorescence intensity of the PCR reaction liquid was measured every 5 cycles. The PCR was continued up to 40 cycles.

The fluorescence intensity was detected as in example 1.

Figure 6:
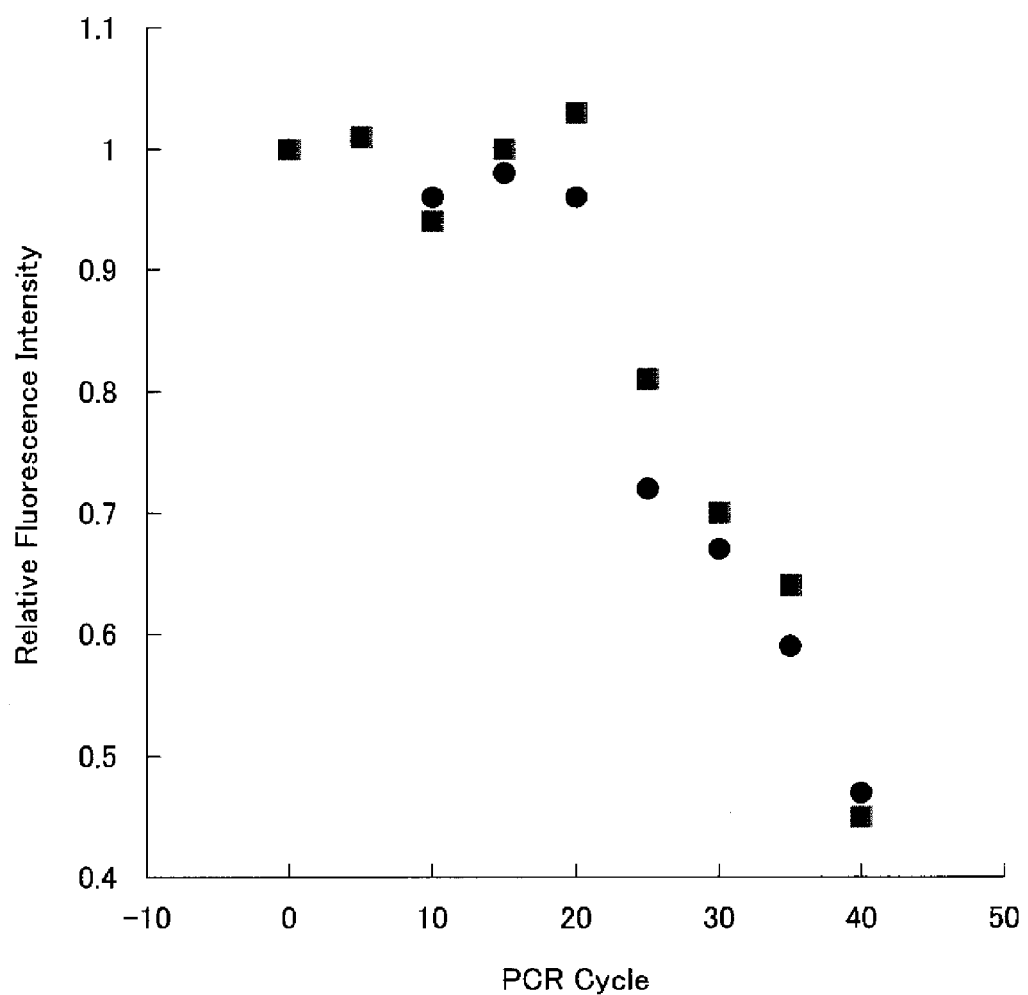

FIG. 6 shows measurements of the fluorescence intensity made every 5 cycles.

FIG. 6 shows relative fluorescence intensity on the vertical axis and PCR cycle on the horizontal axis. The relative fluorescence intensity is a relative value of the fluorescence intensity measurement made every 5 cycles where the fluorescence intensity of the reaction liquid after 0 cycles, that is, before the PCR is started is taken to be 1. Sold circles indicate results of the PCR using takei 5. Solid squares indicate results of the PCR using takei 18.

As can be appreciated from FIG. 6, the relative fluorescence intensity decreased with an increase in the PCR cycle. The decrease occurred because the hairpin structure of takei 5 and takei 18 was linearized in the PCR and lost cytosine bulges. FIG. 6 demonstrates that PCR amplification can be confirmed by detecting a decrease in the fluorescence intensity. FIG. 6 also demonstrates that when either takei 5 or takei 18 is used, amplification of a nucleic acid can be confirmed properly by carrying out at least 25 cycles of PCR.

Example 4

A comparison was made in this example between results of PCR using the hairpin primer in accordance with the present invention and results of PCR using a primer containing no hairpin structure.

In the example, takei 5, takei 18, and takei 18-4 were used as the reverse primer. The DNA having the base sequence according to SEQ ID NO 11 ("M13RV") was used as the reverse primer with no hairpin structure.

M13M3 was used as the forward primer for all the above reverse primers.

Table 4 shows the composition of a PCR reaction liquid used in the example.

TABLE 4

|  | Final Concentration | Amount Added | Concentration of Solution Added |
| --- | --- | --- | --- |
| Forward Primer | 0.5 μM | 10 μL | 10 μM |
| Reverse Primer | 0.5 μM | 10 μL | 10 μM |
| pUC 18 | 50 pM | 20 μL | 1 μg/1 μL |
| DANP | 20 μM | 40 μL | 100 μM |
| Taq mix | — | 100 μL | — |

Water was added to the components in Table 4 to make the total quantity 200 μL. "Taq mix" in Table 4 is the Taq DNA polymerase which came in a Taq PCR Master Mix Kit package (manufactured by QIAGEN). Furthermore, 20 μM of DANP was added as the bulge-binding fluorescent molecule, similarly to example 1.

Temperature conditions for the PCR were 35 cycles of 98° C. for 10 seconds, 55° C. for 30 seconds, and 72° C. for 30 seconds, followed by 4° C. during storage.

The fluorescence intensity was detected as in example 1.

Before the PCR, the fluorescence intensity of the PCR reaction liquid was measured. The PCR reaction liquid was then subjected directly to the PCR. After the PCR was terminated, the fluorescence intensity of the PCR reaction liquid was measured. Table 5 shows the pre PCR and post-PCR measurements of the fluorescence intensity of the reaction liquid.

TABLE 5

|  | Primer | | | |
| --- | --- | --- | --- | --- |
| Cycle | M13RV | takei 5 | takei 18 | takei 18-4 |
| 0 | 531 | 2253 | 2419 | 2752 |
| 35 | 668 | 1674 | 2046 | 1851 |
| Ratio | 1.258 | 0.743 | 0.8458 | 0.6726 |

"Ratio" in Table 5 is equal to FI(35) divided by FI(0), where FI(0) is the pre-PCR fluorescence intensity and FI(35) is the post-PCR fluorescence intensity. The fluorescence intensity slightly increased by the PCR using M13RV. This is attributable to the double-stranded DNA produced by the PCR.

The PCR products obtained by the PCR using M13RV, takei 5, takei 18, and takei 18-4 as the reverse primer were subjected to polyacrylamide gel electrophoresis. Results of the polyacrylamide gel electrophoresis are shown in FIG. 7.

Figure 7:
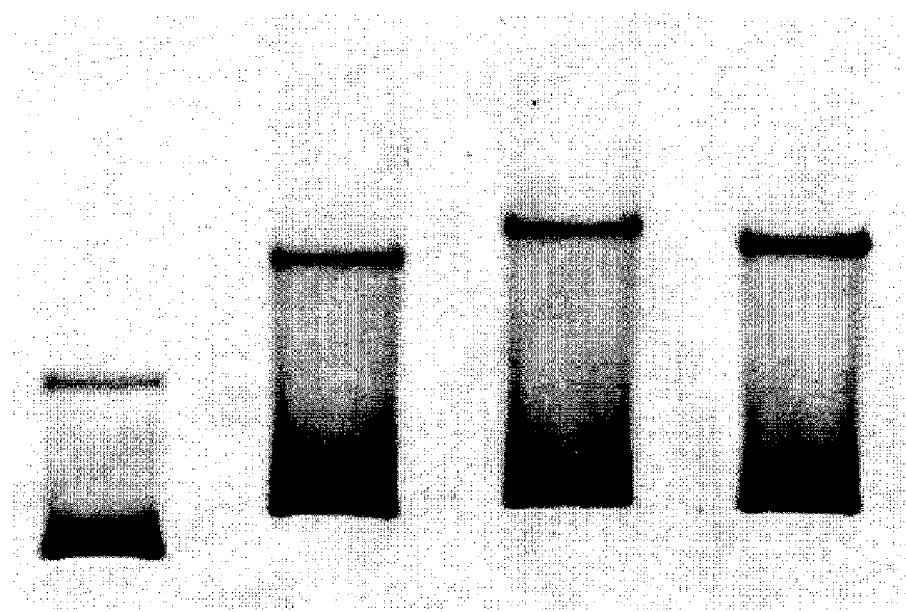

The bands in FIG. 7 were obtained from amplified DNA fragments produced by the PCR using, from left to right, M13RV, takei 5, takei 18, and takei 13-4 as the reverse primer.

As can be appreciated from FIG. 7, the PCR products produced with takei 5, takei 18, and takei 18-4 were longer by the length corresponding to the base sequence forming the hairpin structure than the PCR product produced with M13RV as the reverse primer.

Example 5

It was examined in this example how PCR cycles are related to efficiency of nucleic acid amplification in allele specific PCR using the hairpin primer in accordance with the present invention.

In the example, takei 18-4 (hairpin primer in accordance with the present invention), a primer obtained from takei 18-4 by substituting A for the base at the 3' end (takei 18-4A), a primer obtained from takei 18-4 by substituting G for the base at the 3' end (takei 18-40), and a primer obtained from takei 18-4 by substituting T for the base at the 3' end (takei 18-4T) were used as the reverse primer. M13RV was also used for comparison. FIG. 8 is a schematic illustration of the base sequence and structure of takei 18-4, takei 18-4A, takei 18-40, and takei 18-4T.

M13M3 was used as the forward primer for all the above reverse primers.

Table 6 shows the composition of a PCR reaction liquid used in the example.

TABLE 6

|  | Final Concentration | Amount Added | Concentration of Solution Added |
| --- | --- | --- | --- |
| Forward Primer | 0.5 μM | 15 μL | 10 μM |
| Reverse Primer | 0.5 μM | 15 μL | 10 μM |
| pUC 18 | 50 pM | 30 μL | 1 ng/1 μM |
| DANP | 20 μM | 60 μL | 100 μM |
| Taq mix | — | 150 μL | — |
| Water | — | 30 μL | — |

"Taq mix" in Table 6 is the Taq DNA polymerase which came in a Taq PCR Master Mix Kit package (manufactured by QIAGEN)

The PCR was carried out at 98° C. for 10 seconds, 55° C. for 30 seconds, and 72° C. for 30 seconds. The fluorescence intensity of the PCR reaction liquid was measured before performing the PCR on the liquid. The PCR reaction liquid was then subjected directly to the PCR. Thereafter, the fluorescence intensity of the PCR reaction liquid was measured every 5 cycles. The PCR was continued up to 40 cycles.

The fluorescence intensity was detected as in example 1.

Figure 9:
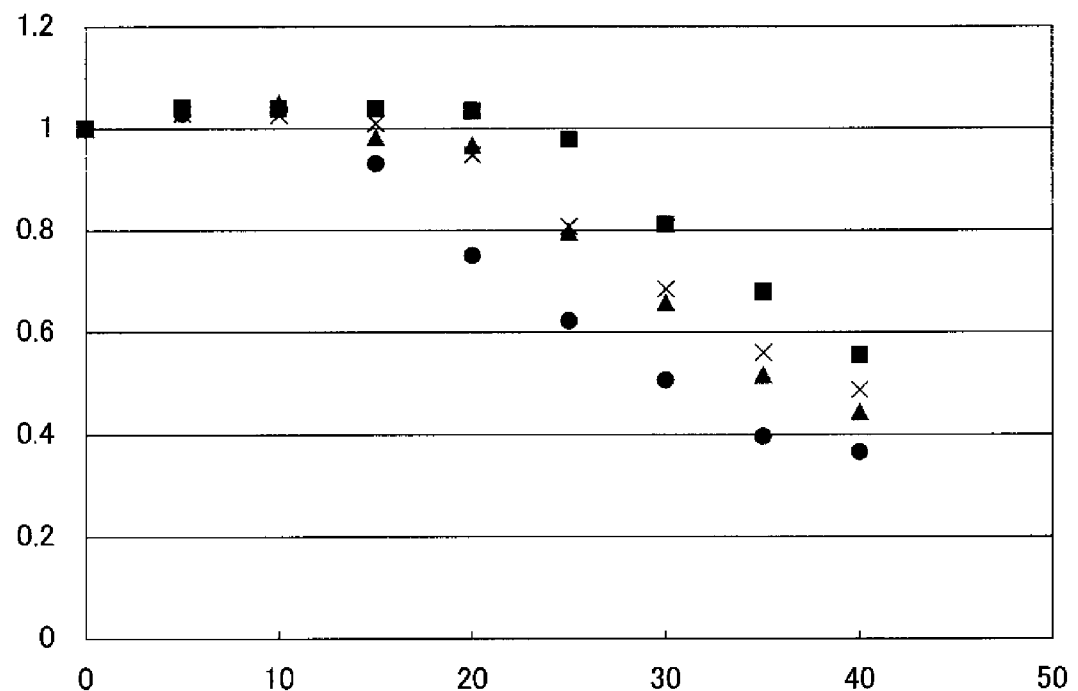

Table 7 and FIG. 9 show measurements of the fluorescence intensity for the PCR using takei 18-4, takei 18-4A, takei 18-4G, and takei 18-4T as the reverse primer.

TABLE 7

| Primer | PCR Cycle | | | | | | | | |
|---|---|---|---|---|---|---|---|---|---|
|  | 0 | 5 | 10 | 15 | 20 | 25 | 30 | 35 | 40 |
| takei 18-4 | 1 | 1.03 | 1.039 | 0.932 | 0.751 | 0.622 | 0.507 | 0.397 | 0.367 |
| takei 18-4A | 1 | 1.043 | 1.039 | 1.039 | 1.035 | 0.979 | 0.811 | 0.679 | 0.555 |
| takei 18-4G | 1 | 1.041 | 1.049 | 0.983 | 0.968 | 0.796 | 0.657 | 0.517 | 0.445 |
| takei 18-4T | 1 | 1.03 | 1.027 | 1.01 | 0.949 | 0.807 | 0.684 | 0.56 | 0.488 |

FIG. 9 shows relative fluorescence intensity on the vertical axis and PCR cycle on the horizontal axis. Sold circles, solid squares, solid triangles, and crosses indicate results of the PCR using takei 18-4. takei 18-4A. takei 18-4G, and takei 18-4T respectively.

As can be appreciated from Table 7 and FIG. 9, the fluorescence intensity decreased by fewer PCR cycles when takei 18-4 was used than when the other reverse primers were used. It was confirmed that the fluorescence intensity decreased also by an increase in the PCR cycle when takei 18-4A, takei 18-4G, and takei 18-4T were used. This is due to an alleged shortcoming of the allele specific PCR that even if a primer contains bases not complementary to the target nucleic acid, the PCR progresses using DNA as a template once part of the primer is annealed to a template DNA, a DNA polymerase recognizes this, and the PCR progresses to synthesize DNA.

However, in the example, the relative fluorescence intensity decreased to 0.75 by 20 cycles of PCR using takei 18-4, whereas the relative fluorescence intensity remained at about 1 if the other reverse primers were used. The difference demonstrates that in the allele specific PCR using primers obtained from takei 18-4 and takei 18-4 by substituting the base at the 3' end for another base, 20 cycles of the PCR is sufficient to determine if the base located at the 3' end of the nucleic acid subjected to the PCR has mutated.

Next, the PCR products obtained by the PCR using takei 18-4, takei 18-4A, takei 18-4G, takei 18-4T, and M13RV as the reverse primer were subjected to polyacrylamide gel electrophoresis as in example 4.

Figure 10:
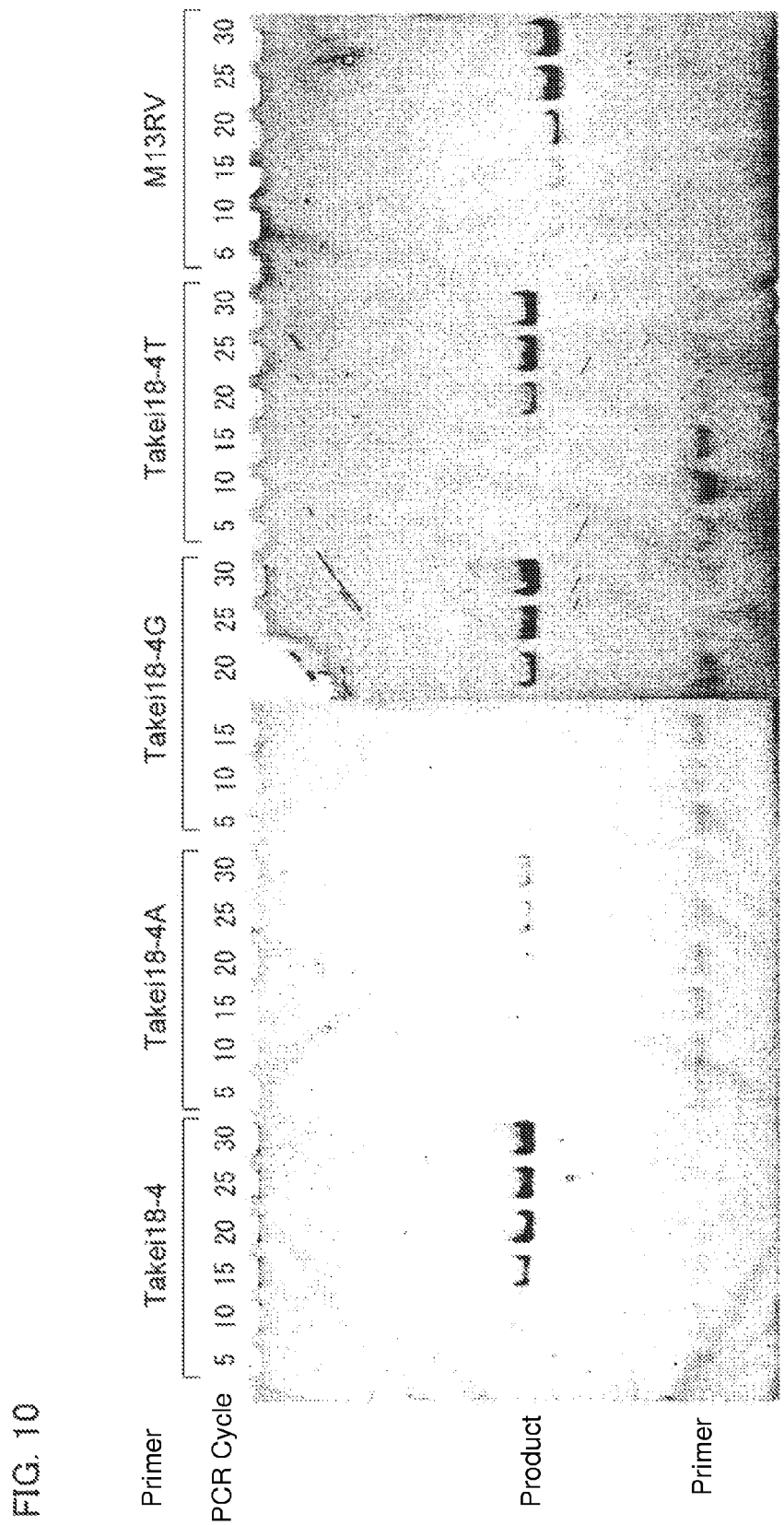

Results of the polyacrylamide gel electrophoresis are shown in FIG. 10. The numbers on the lanes in FIG. 10 are PCR cycles for the PCR using the reverse primers. The bands on the same line with "product" were derived from PCR products obtained by the PCR. The bands on the same line with "primer" were derived from the primers which were remained unused in the PCR.

As can be appreciated from FIG. 10, the nucleic acid was amplified by fewer PCR cycles when takei 18-4 was used than when the other reverse primers were used. In addition, it was confirmed that the PCR products produced with takei 18-4, takei 18-4A, takei 18-4G, and takei 18-4T were longer by the length corresponding to the base sequence forming the hairpin structure than the PCR product produced with M13RV as the reverse primer.

Example 6

It was examined in this example how PCR cycles are related to efficiency of nucleic acid amplification in allele specific PCR using, as well as the hairpin primer in accordance with the present invention, a competitor primer.

In the example, takei 18-4 and takei 18-4A (hairpin primer in accordance with the present invention) were used as the reverse primer.

M13M3 was used as the forward primer for all the above reverse primers.

As the competitor primer, M13RV was used in the PCR using takei 18-4A as the reverse primer, and a primer obtained from M13RV by substituting A for the base at the 3' end ("M13RVA") was used in the PCR using takei 18-4 as the reverse primer. pUC 18, the template DNA for the PCR, contained G at the site corresponding to the 3' end of the reverse primer.

Table 8 and Table 9 show the compositions of PCR reaction liquids used in the example.

TABLE 8

|  | Final Concentration | Amount Added | Concentration of Solution Added |
|---|---|---|---|
| Forward Primer | 0.5 µM | 15 µL | 10 µM |
| Reverse Primer | 0.5 µM | 15 µL | 10 µM |
| pUC 18 | 50 pM | 30 µL | 1 ng/1 µM |
| DANP | 20 µM | 60 µL | 100 µM |
| Taq mix | — | 150 µL |  |
| Water | — | 30 µL |  |

TABLE 9

|  | Final Concentration | Amount Added | Concentration of Solution Added |
|---|---|---|---|
| Forward Primer | 0.5 µM | 15 µL | 10 µM |
| Hairpin Primer | 0.5 µM | 15 µL | 10 µM |
| Competitor Primer | 2.5 µM | 7.5 µL | 100 µM |
| pUC 18 | 50 pM | 30 µL | 1 ng/1 µM |
| DANP | 20 µM | 60 µL | 100 µM |
| Taq mix | — | 150 µL | — |
| Water | — | 22.5 µL | — |

Table 8 shows the composition of the PCR reaction liquid used in the PCR which did used no competitor primer. Table 9 shows the composition of the PCR reaction liquid used in the PCR which used a competitor primer. As shown in Table 9, the mole ratio of the reverse primer to the competitor primer was set to 1:5.

"Taq mix" in Table 8 and Table 9 is the Taq DNA polymerase which came in a Taq PCR Master Mix Kit package (manufactured by QIAGEN).

The PCR was carried out by first heating at 95° C. for 1 minute, followed by cycles of 95° C. for 10 seconds, 55° C. for 30 seconds, and 72° C. for 30 seconds. The fluorescence intensity of the PCR reaction liquid was measured before performing the PCR on the liquid. The PCR reaction liquid was then subjected directly to PCR. Thereafter, the fluorescence intensity of the PCR reaction liquid was measured every 5 cycles. The PCR was continued up to 40 cycles.

The fluorescence intensity was detected as in example 1.

Figure 11:
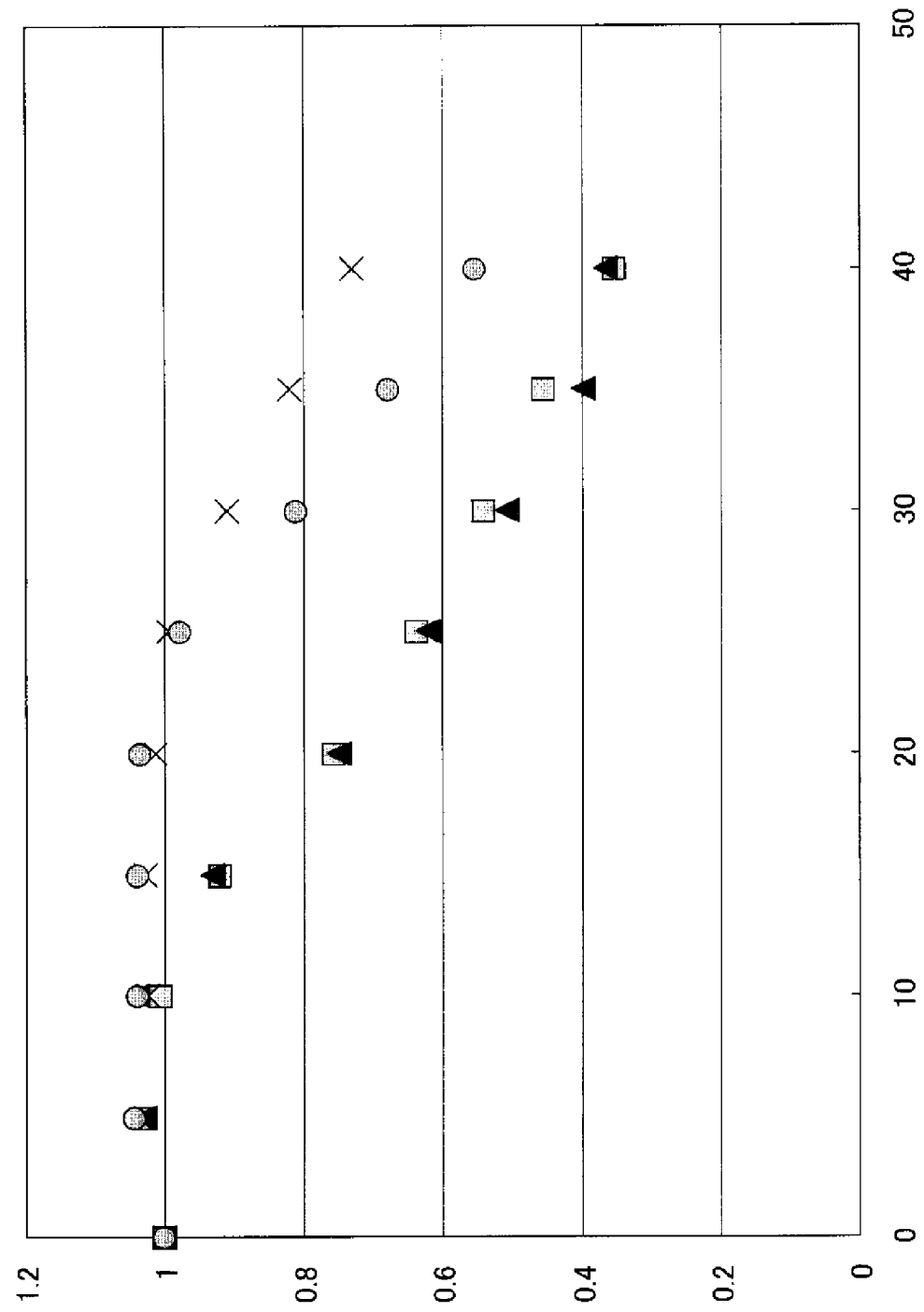

FIG. 11 shows measurements of the fluorescence intensity for the PCR.

FIG. 11 shows relative fluorescence intensity on the vertical axis and PCR cycle on the horizontal axis. Solid squares, crosses, solid triangles, and sold circles indicate results of the PCR using takei 18-4 and M13RVA, takei 18-4A and M13RV, takei 18-4, and takei 18-4A respectively.

As can be appreciated from FIG. 11, no significant difference was observed in decreases in the fluorescence intensity between when only takei 18-4 was used and when takei 18-4 and M13RVA were used together. These results demonstrate that M13RVA did not disrupt the PCR proceeding with takei 18-4. Furthermore, the fluorescence intensity decreased more slowly, that is, more PCR cycles were needed to reduce the fluorescence intensity to the same level, when takei 18-4A and M13RV were used than when only takei 18-4A was used. The results demonstrate that M13RV was more preferably consumed in the PCR than takei 18-4A, preventing the PCR from proceeding by consuming takei 18-4A.

Next, the PCR products obtained by the PCR using takei 18-4 and M13RVA, and takei 18-4A and M13RV were subjected to polyacrylamide gel electrophoresis as in example 4.

Figure 12:
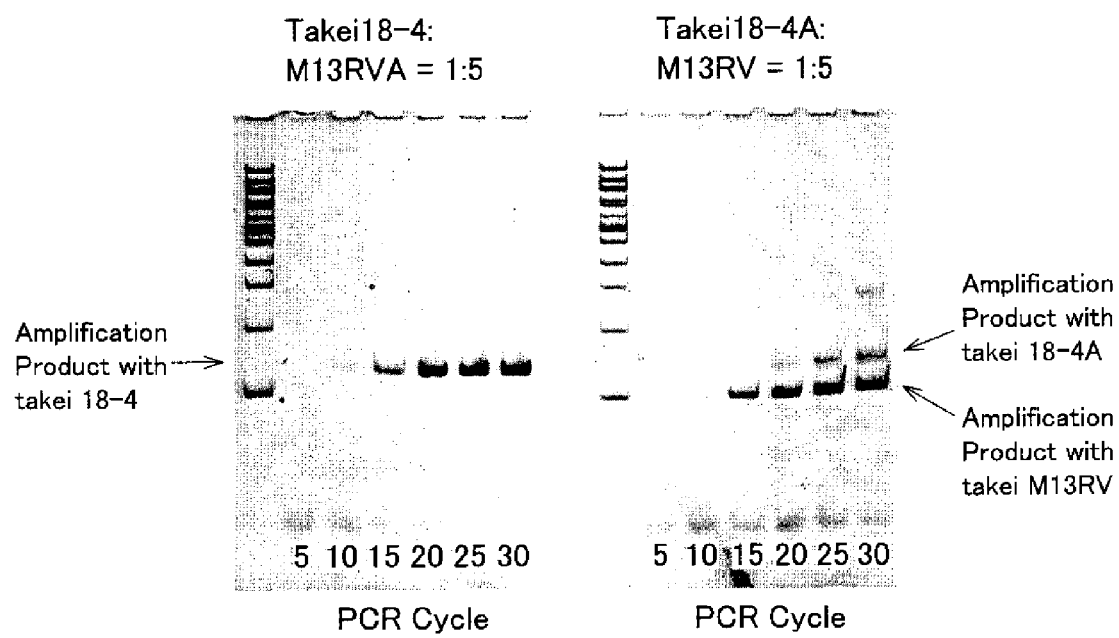

Results of the polyacrylamide gel electrophoresis are shown in FIG. 12. The reverse and competitor primers used, and their mole ratio are given on each polyacrylamide gel in FIG. 12. Furthermore, for each polyacrylamide gel, the leftmost lane is a DNA ladder and the numbers below each lane indicate PCR cycles.

As can be appreciated from FIG. 12, the nucleic acid was amplified by takei 18-4, but not by M13RVA, in the PCR using takei 18-4 and M13RVA. In contrast, in the PCR using takei 18-4A and M13RV, the nucleic acid was amplified by M13RV in relatively few PCR cycles and by takei 18-4A only after relatively many PCR cycles. These results also demonstrate that M13RV was more preferably consumed in the PCR than takei 18-4A.

The DNA fragment in accordance with the present invention, as described in the foregoing, is a single-stranded DNA fragment containing a hairpin structure which in turn contains a bulge, wherein the DNA fragment is used as being attached to a 5 end of a primer used in nucleic acid amplification.

If a target nucleic acid is amplified in a nucleic acid amplification reaction by using a nucleic acid amplification primer to which the DNA fragment in accordance with the present invention is attached, the hairpin structure of the DNA fragment is linearized and lost. As a result, the bulge disappears.

Therefore, by detecting the bulge with publicly known bulge-binding molecules, the quantity of the nucleic acid amplification primer attaching to the DNA fragment in accordance with the present invention can be compared before and after the nucleic acid amplification reaction, and the amplification of the nucleic acid can be confirmed. Therefore, the amplification of the nucleic acid can be confirmed more quickly than by electrophoresis or staining an amplified PCR product. In addition, no electrophoresis device or PCR product staining reagent is needed.

The present invention enables quick, convenient, inexpensive, and high sensitivity confirmation of amplification of nucleic acid in nucleic acid amplification reaction.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The nucleic acid amplification confirmation method in accordance with the present invention is applicable in any PCR-related industries, including bioassay involving gene analysis and gene monitoring. The SNP analysis method in accordance with the present invention is applicable in, for example, the clinical test, pharmaceutical, and other industries related with tailor-made medical care.

Sequence Listing Free Text
G20070017 Sequence Listing.txt

The invention claimed is:

1. A hairpin primer being an isolated DNA fragment for a polymerase chain reaction (PCR), comprising:
   a nucleic acid fragment having a hairpin structure; and
   a primer segment,
   wherein:
   the hairpin structure contains bulges;
   the bulges are cytosine bulges;
   said nucleic acid fragment is attached to a 5' end of the primer segment; and
   the hairpin primer contains any one of base sequences according to SEQ ID NOs 1 to 5.

2. A method of confirming amplification of a nucleic acid in a nucleic acid amplification reaction, said method comprising:
   preparing a nucleic acid amplification reaction liquid containing a set of primers at least one of which is the hairpin primer of claim 1;
   quantifying the hairpin primer in the nucleic acid amplification reaction liquid prior to amplification using bulge-binding molecules;
   initiating a nucleic amplification reaction in the nucleic amplification reaction liquid;
   quantifying the hairpin primer in the nucleic acid amplification reaction liquid during and/or after amplification using bulge-binding molecules.

3. The method as set forth in claim 2, wherein the bulge-binding molecules are a compound with a naphthyridine ring.

4. The method as set forth in claim 3, wherein the compound with a naphthyridine ring is a 2,7-diamino naphthyridine derivative of chemical formula 1:

Chem. 1

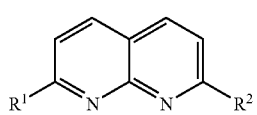

(1)

where each of $R^1$ and $R^2$, mutually independent, is a primary amine residue, a secondary amine residue, or a tertiary amine residue.

5. The method as set forth in claim 4, wherein the 2,7-diamino naphthyridine derivative is 2,7-diamino-1,8-naphthyridine of chemical formula 2:

Chem. 2

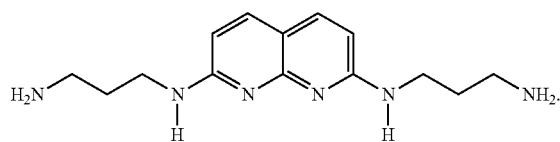

(2)

6. The method as set forth in claim 3, wherein the bulge-binding molecules are added to the nucleic acid amplification reaction liquid prior to amplification.

7. A method of detecting an SNP, said method comprising the step of carrying out the method of claim 2, wherein any one of the set of primers is designed to have a 3' end located at a site where a target SNP is to be detected.

8. The method as set forth in claim 7, wherein the primer designed to have a 3' end located at a site where a target SNP is to be detected is the hairpin primer.

9. The method as set forth in claim 8, wherein:
   the nucleic acid amplification reaction liquid contains a competitor primer;
   the competitor primer is designed to have a 3' end located at the site where the target SNP is to be detected; and
   the competitor primer has, at the 3' end, a base complementary to a base in a mutated nucleic acid where the target SNP is to be detected when the hairpin primer is used to amplify a wildtype nucleic acid and a base complementary to a base in a wildtype nucleic acid where the target SNP is to be detected when the hairpin primer is used to amplify a mutated nucleic acid.

10. A reagent kit for confirming amplification of a nucleic acid in a nucleic acid amplification reaction, said reagent kit comprising at least the hairpin primer of claim 1.

* * * * *

SEQUENCE LISTING

```
<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
atcaaacaca cttttgttgt cttgat                                          26

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2
atcaacatct caacttttgt ctgaatgtct gat                                  33

<210> SEQ ID NO 3
<211> LENGTH: 28
<212> TYPE: DNA
<213> ORGANISM: Artificial Sequence
<220> FEATURE:
```

```
<223> OTHER INFORMATION: Description of Artificial Sequence:Artificially
      Synthesized Primer Sequence

<400> SEQUENCE: 3
atcatctaca acttttgtct gtaatgat                                              28

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
catccaaaca accattttg gttgtcttgg atg                                         33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
catccattca accattttg gttgacatgg atg                                         33

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
atcaaacaca cttttgttgt cttgatcagg aaacagctat gac                             43

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
atcaacatct caacttttgt ctgaatgtct gatcaggaaa cagctatgac                      50

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
atcatctaca acttttgtct gtaatgatca ggaaacagct atgac                           45

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence:Artificially
```

Synthesized Primer Sequence

<400> SEQUENCE: 9
catccaaaca accattttg gttgtcttgg atgcaggaaa cagctatgac        50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
catccattca accattttg gttgacatgg atgcaggaaa cagctatgac        50

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
caggaaacag ctatgac        17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
gtaaaacgac ggccagt        17

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
atcatctaca acttttgtct gtaatgatca ggaaacagct atgaa        45

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
atcatctaca acttttgtct gtaatgatca ggaaacagct atgag        45

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 15
atcatctaca acttttgtct gtaatgatca ggaaacagct atgat              45

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:Artificially
      Synthesized Primer Sequence
<220> FEATURE:
<221> NAME/KEY: misc_feature
<222> LOCATION: 5, 6, 7, 8
<223> OTHER INFORMATION: n = A,T,C or G

<400> SEQUENCE: 16
ccaannnntt gg                                                  12
```